US006991911B2

(12) United States Patent
Zheng et al.

(10) Patent No.: US 6,991,911 B2
(45) Date of Patent: Jan. 31, 2006

(54) ASSAY FOR ENTACTOGENS

(75) Inventors: Yi Feng Zheng, Wilmington, DE (US); Hshiou-ting Liu, Milpitas, CA (US)

(73) Assignee: Dade Behring Inc., Deerfield, IL (US)

( * ) Notice: Subject to any disclaimer, the term of this patent is extended or adjusted under 35 U.S.C. 154(b) by 91 days.

(21) Appl. No.: 10/736,005

(22) Filed: Dec. 15, 2003

(65) Prior Publication Data
US 2005/0130244 A1 Jun. 16, 2005

(51) Int. Cl.
- *G01N 33/53* (2006.01)
- *G01N 33/531* (2006.01)
- *C07K 16/00* (2006.01)
- *C07K 17/02* (2006.01)
- *C07D 317/58* (2006.01)

(52) U.S. Cl. .............. 435/7.9; 435/961; 435/975; 435/7.1; 435/188; 436/544; 436/546; 530/388.9; 530/389.8; 530/402; 530/403; 530/405; 424/175.1; 549/444; 549/443; 548/526

(58) Field of Classification Search ........... 549/444, 549/443; 435/961, 7.1, 7.9, 188, 975; 530/388.9, 530/389.8, 403, 405, 402; 436/546, 545, 436/544; 424/175.1; 548/526
See application file for complete search history.

(56) References Cited

U.S. PATENT DOCUMENTS

| | | | |
|---|---|---|---|
| 1,879,003 A | 9/1932 | Alles | 564/381 |
| 1,921,424 A | 8/1933 | Nabenhauer | 167/58 |
| 2,344,356 A | 3/1944 | Hildebrandt | 260/570.8 |
| 3,117,160 A | 1/1964 | Holland | 260/570.8 |
| 3,547,999 A | 12/1970 | Shulgin | 260/570.8 |
| 3,709,868 A | 1/1973 | Spector | 260/121 |
| 3,758,691 A | 9/1973 | Carlsson et al. | 424/330 |
| 3,763,218 A | 10/1973 | Kaiser et al. | 260/471 A |
| 3,766,162 A | 10/1973 | Spector | 260/112 R |
| 3,775,536 A | 11/1973 | Spector et al. | 424/1 |
| 3,847,950 A | 11/1974 | Suh et al. | 260/340.5 |
| 3,867,366 A | 2/1975 | Rubenstein et al. | 260/121 |
| 3,875,011 A | 4/1975 | Rubenstein et al. | 195/99 |
| 3,911,016 A | 10/1975 | Klingler et al. | 260/570.8 R |
| 3,995,021 A | 11/1976 | Gross | 424/1.5 |
| 3,996,344 A | 12/1976 | Gross | 424/1.5 |
| 4,016,146 A | 4/1977 | Soares | 260/112 R |
| 4,022,878 A | 5/1977 | Gross | 424/1.5 |
| 4,036,823 A | 7/1977 | Soares | 260/112 R |
| 4,041,076 A | 8/1977 | Avenia et al. | 260/559 A |
| 4,058,642 A | 11/1977 | Renth et al. | 424/330 |
| 4,064,228 A | 12/1977 | Gross | 424/1 |
| 4,073,798 A | 2/1978 | Suh | 260/340.5 R |
| 4,097,586 A | 6/1978 | Gross | 424/1 |
| 4,129,598 A | 12/1978 | Giudicelli et al. | 260/570.8 R |
| 4,218,539 A | 8/1980 | Weltman | 435/188 |
| 4,220,565 A | 9/1980 | Katz | 260/6 |
| 4,329,281 A | 5/1982 | Christenson et al. | 260/112 B |
| 4,595,656 A | 6/1986 | Allen et al. | 435/7 |
| 4,680,338 A | 7/1987 | Sundoro | 525/54.1 |
| 4,686,181 A | 8/1987 | Dona | 435/7 |
| 4,760,142 A | 7/1988 | Primes et al. | 544/287 |
| 4,843,147 A | 6/1989 | Levy et al. | 530/391 |
| 4,847,195 A | 7/1989 | Khanna et al. | 435/7 |
| 4,868,132 A | 9/1989 | Byrnes et al. | 436/546 |
| 4,952,336 A | 8/1990 | Brynes et al. | 252/301.16 |
| 4,990,443 A | 2/1991 | Huber et al. | 435/7.9 |
| 5,026,827 A | 6/1991 | Miyazaki et al. | 530/405 |
| 5,101,015 A | 3/1992 | Byrnes et al. | 530/363 |
| 5,135,863 A | 8/1992 | Hu et al. | 435/188 |
| 5,145,791 A | 9/1992 | Zeitvogel et al. | 436/546 |
| 5,198,587 A | 3/1993 | Imai et al. | 564/374 |
| 5,227,472 A | 7/1993 | Yoshioka | 530/403 |
| 5,233,025 A | 8/1993 | Miyazaki et al. | 530/388.9 |
| 5,256,409 A | 10/1993 | Blincko | 424/85.8 |
| 5,262,333 A | 11/1993 | Heiman et al. | 436/537 |
| 5,266,720 A | 11/1993 | Gallacher et al. | 560/60 |
| 5,270,166 A | 12/1993 | Parsons et al. | 435/7.4 |
| 5,294,638 A | 3/1994 | Hell et al. | 514/452 |
| 5,328,828 A | 7/1994 | Hu et al. | 435/7.9 |
| 5,336,621 A | 8/1994 | Primes et al. | 436/534 |
| 5,354,693 A | 10/1994 | Byrnes et al. | 436/537 |
| 5,372,949 A | 12/1994 | Zeitvogel et al. | 436/546 |
| 5,373,092 A | 12/1994 | Gallacher et al. | 435/7.93 |
| 5,424,204 A | 6/1995 | Aoyama et al. | 435/188 |
| 5,470,997 A | 11/1995 | Buechler et al. | 558/254 |
| 5,492,841 A | 2/1996 | Craig | 436/534 |
| 5,501,987 A | 3/1996 | Ordonez et al. | 436/534 |

(Continued)

FOREIGN PATENT DOCUMENTS

DE 2844427 4/1980

(Continued)

*Primary Examiner*—Mary E. Ceperley
*Assistant Examiner*—Shafiqul Haq
(74) *Attorney, Agent, or Firm*—Theodore J. Leitereg

(57) ABSTRACT

Methods, compositions and kits are disclosed. The methods are directed to determining the presence of entactogen analytes such as, for example, 3,4-methylenedioxyamphetamine (MDA), 3,4-methylenedioxy-methamphetamine (MDMA), 3,4-methylenedioxy-ethylamphetamine (MDEA) and 4-hydroxy-3-methoxy-methamphetamine (HMMA). The method comprises providing in combination in a medium (i) a sample suspected of containing the compound and (ii) an antibody raised against a compound of Formula I that comprises a protein. The medium is examined for the presence a complex comprising the compound and the antibody where the presence of such as complex indicates the presence of the compound in the sample. In one aspect of the above embodiment, the combination further comprises a label conjugate of the compound Formula I.

37 Claims, 11 Drawing Sheets

U.S. PATENT DOCUMENTS

| | | |
|---|---|---|
| 5,514,559 A | 5/1996 | Markert-Hahn et al. ..... 435/7.92 |
| 5,518,887 A | 5/1996 | Parsons et al. .............. 435/7.1 |
| 5,525,524 A | 6/1996 | Buechler et al. ............ 436/518 |
| 5,610,283 A | 3/1997 | Buechler .................... 530/404 |
| 5,616,503 A | 4/1997 | Self .......................... 436/518 |
| 5,643,732 A | 7/1997 | Strahilevitz ................. 435/7.1 |
| 5,840,588 A | 11/1998 | Strahilevitz ................ 436/518 |
| 5,851,776 A | 12/1998 | Valkirs ....................... 435/7.1 |
| 5,976,812 A | 11/1999 | Huber et al. ................. 435/7.1 |
| 6,033,890 A | 3/2000 | Jakobovits et al. ......... 435/190 |
| 6,090,567 A | 7/2000 | Jakobovits et al. .......... 435/7.9 |
| 6,140,137 A | 10/2000 | Sigler et al. ................ 436/536 |
| 6,214,859 B1 | 4/2001 | Yoneda et al. ............... 514/419 |
| 2003/0170917 A1 | 9/2003 | Hui et al. .................... 436/547 |
| 2003/0175995 A1 | 9/2003 | Hui ........................... 436/547 |

FOREIGN PATENT DOCUMENTS

| | | |
|---|---|---|
| EP | 828880 | 7/1958 |
| EP | 1467560 | 11/1975 |
| EP | 0 183901 A2 | 11/1985 |
| EP | WO 86/05189 | 9/1986 |
| EP | WO 90/15798 | 12/1990 |
| EP | 0 517325 A2 | 6/1992 |
| EP | 1 321772 A1 | 12/2002 |
| EP | 1340981 A2 * | 9/2003 |
| GB | 2361473 A * | 10/2001 |
| JP | 53066417 A | 6/1978 |
| JP | 56125666 A | 10/1981 |
| JP | 63220932 | 9/1988 |
| JP | 2069196 A | 3/1990 |

* cited by examiner

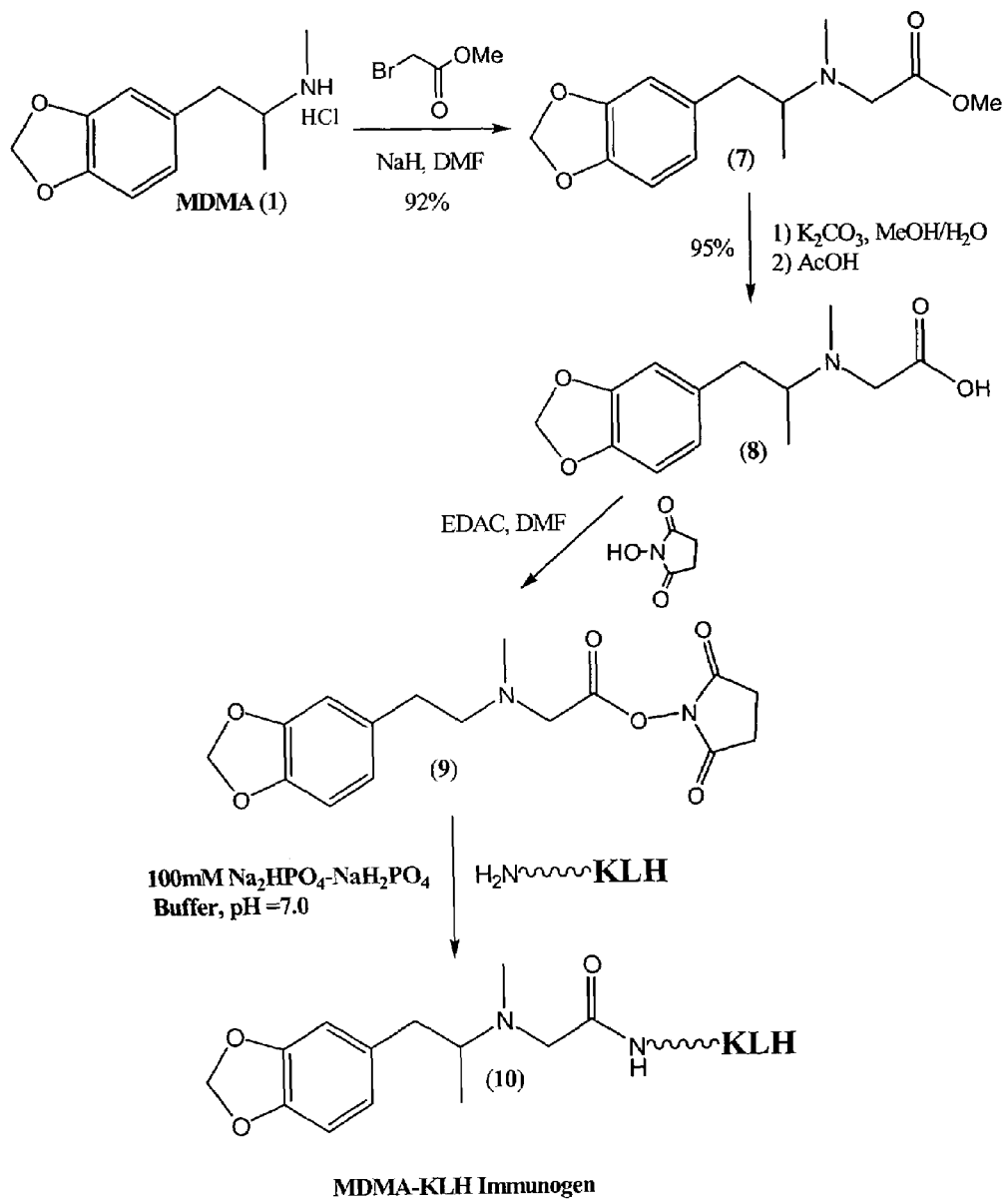
Figure 1. Synthesis of MDMA-KLH Immunogen (10)

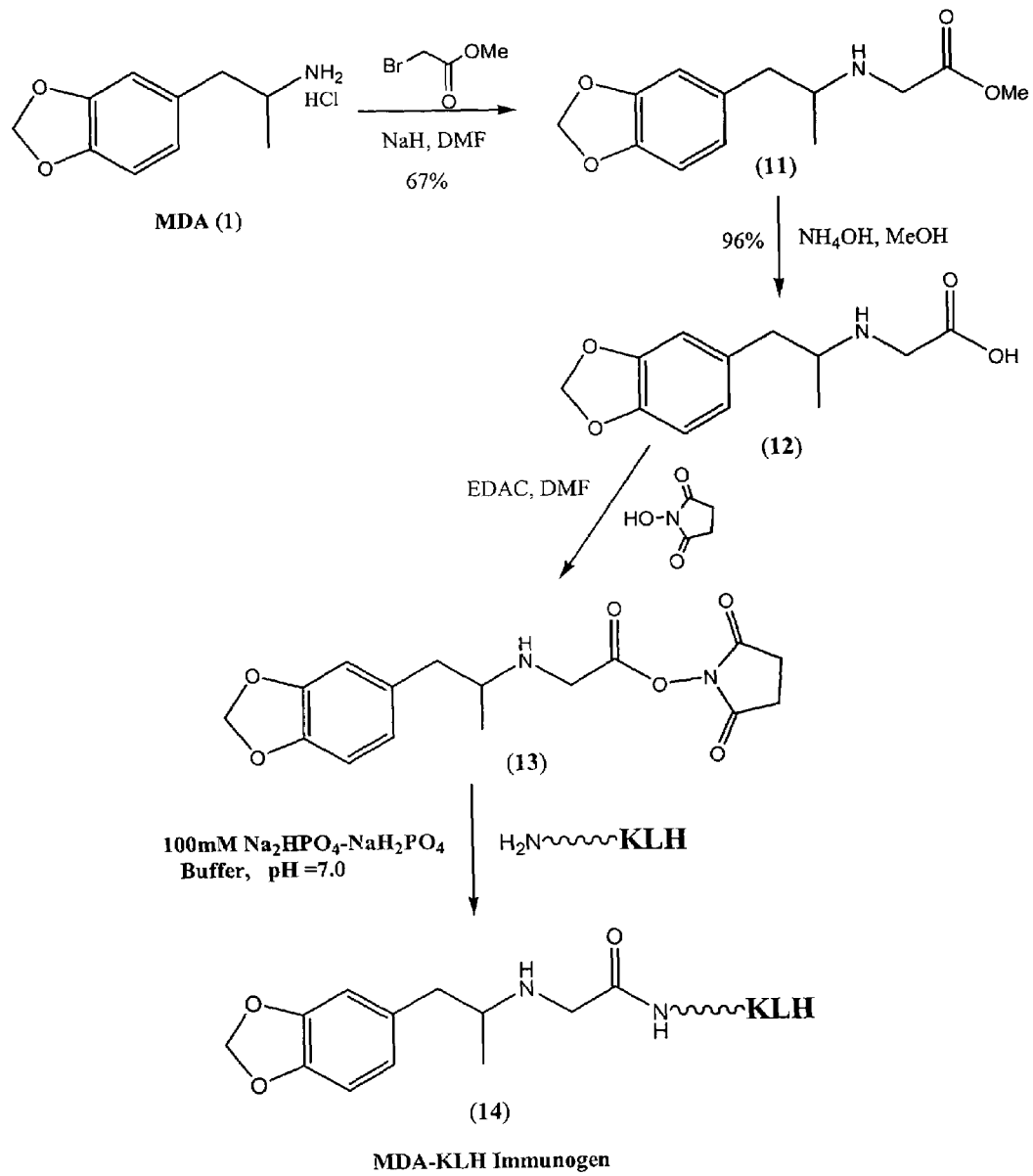
Figure 2. Synthesis of MDA-KLH Immunogen (14)

Figure 3. Synthesis of MDMA Haptens (15)-(17)
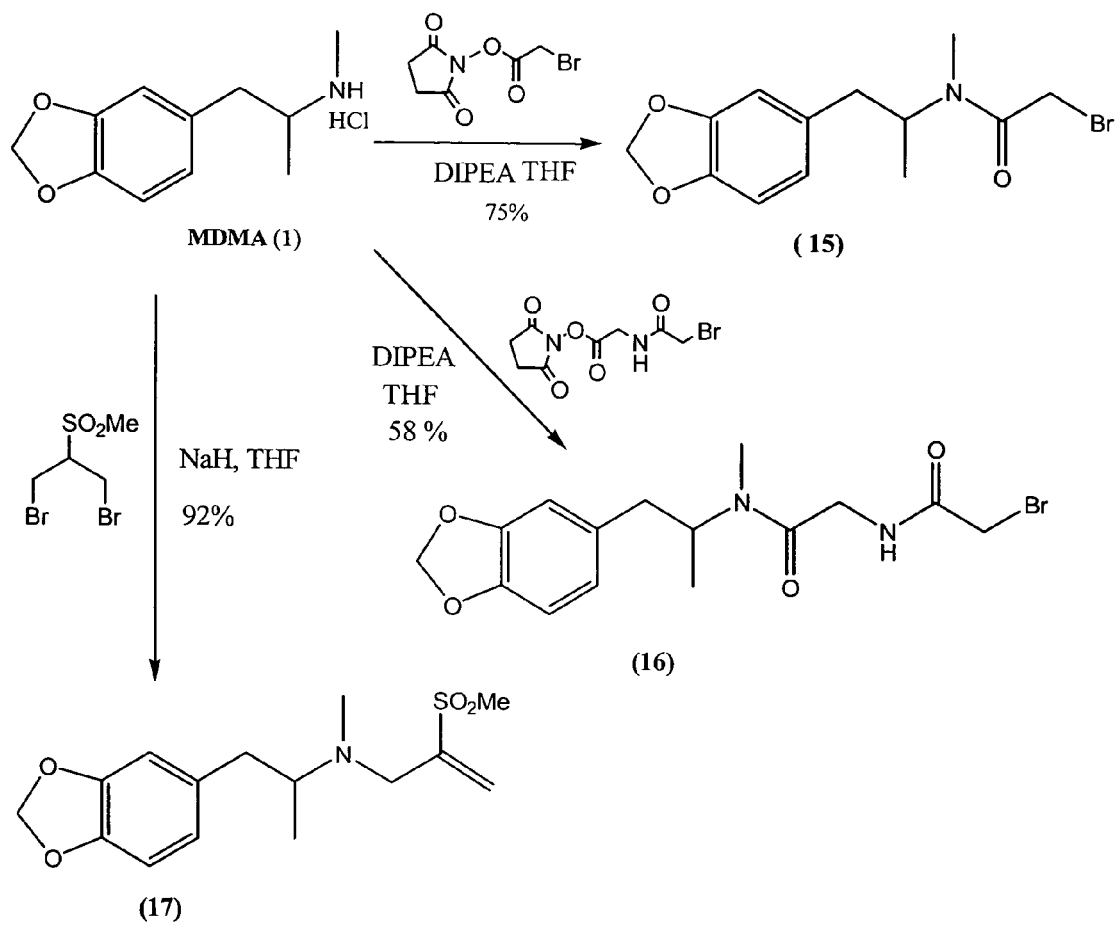

Figure 4A. Synthesis of MDA Haptens (18)-(19)
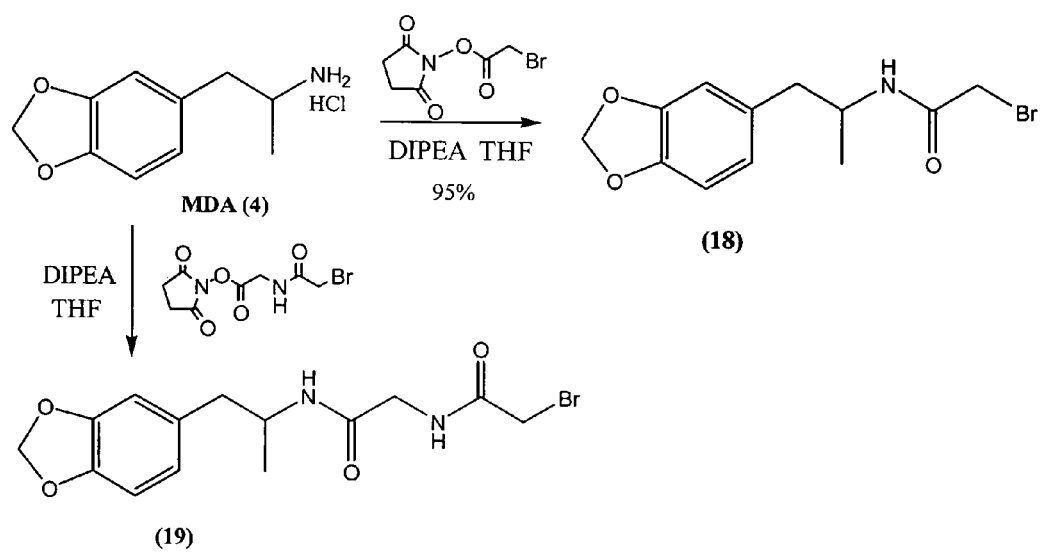
Figure 4B. Synthesis of MDA Hapten (20)
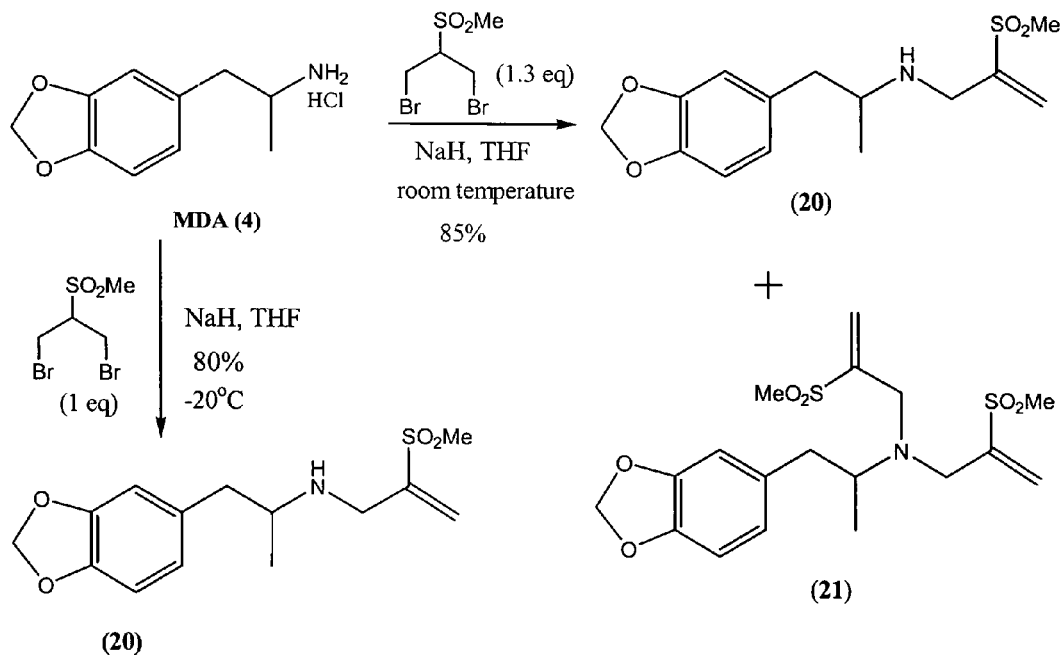

Figure 5. Synthesis of HMMA Intermediate (29) for Immunogen (30)
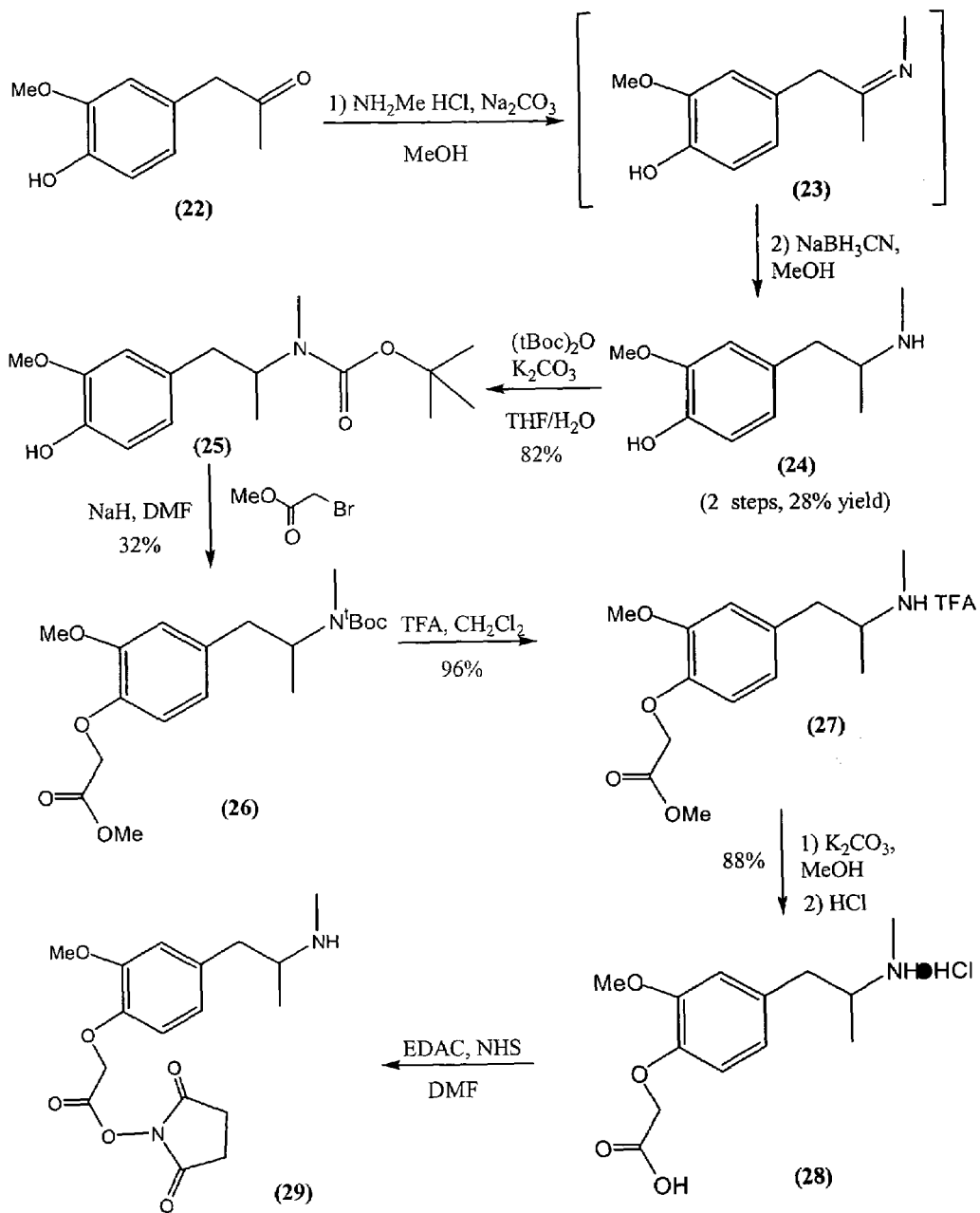

Figure 6. Synthesis of HMMA-KLH Immunogen (30)
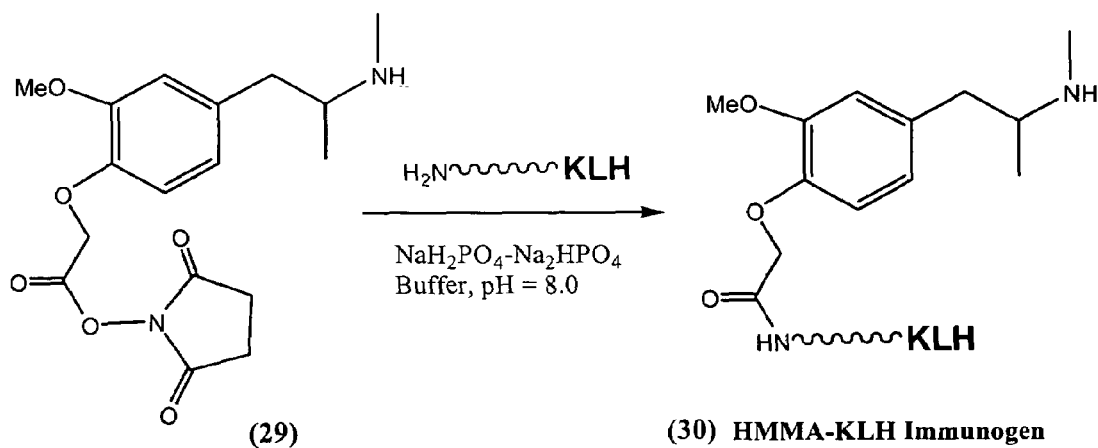

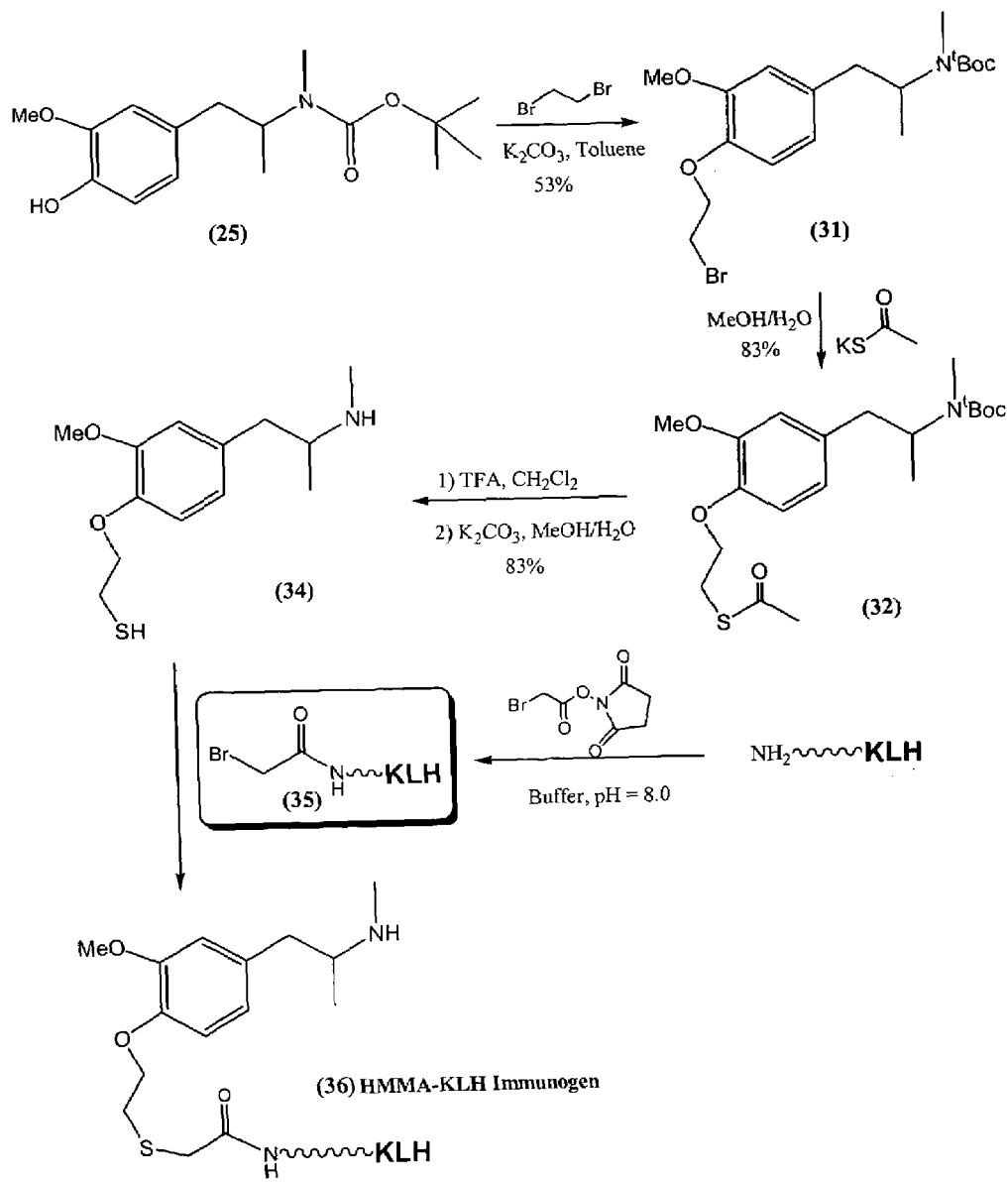
Figure 7. Synthesis of HMMA-KLH Immunogen (36)

Figure 8A. Synthesis of MDMA Hapten (38)
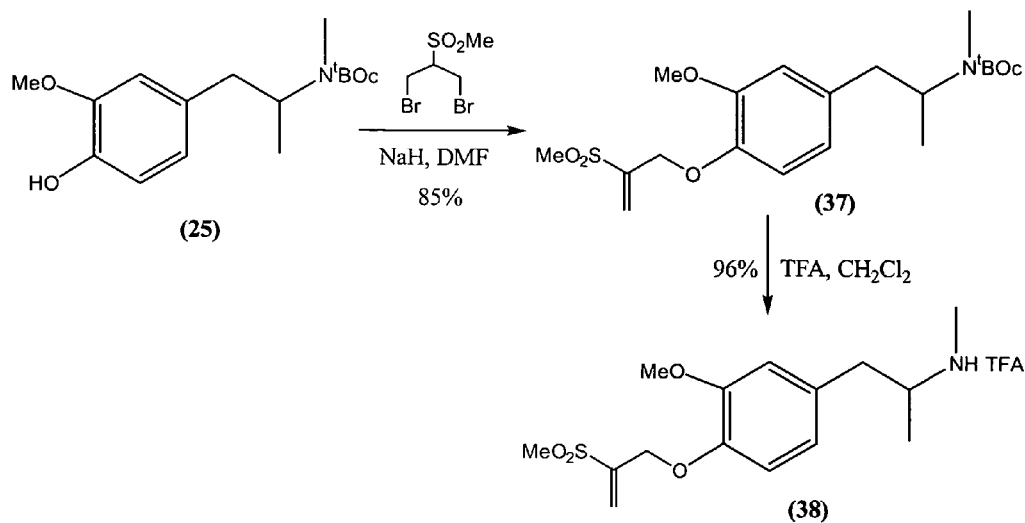
Figure 8B. Synthesis of MDMA Hapten Intermediate (40)
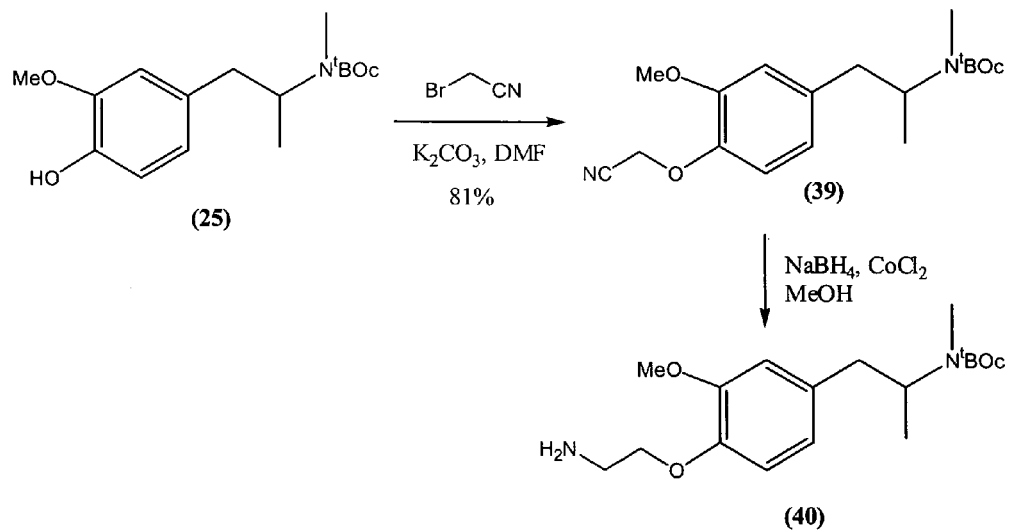

MDMA Recovery by the Ecstasy Assay

| Nominal Ecstasy Concentration (ng/ml) | Ecstasy conc. (ng/ml) |
|---|---|
| 200 | 191 |
| 250 | 241 |
| 375 | 360 |
| 450 | 428 |
| 750 | 730 |
| 1250 | 1222 |
| 1500 | 1478 |

US 6,991,911 B2

ASSAY FOR ENTACTOGENS

BACKGROUND OF THE INVENTION

This invention relates to methods, compositions and kits for detecting the presence and/or amounts of entactogens in samples suspected of containing the same. In particular, the invention relates to haptens, immunogens and assays for 3,4-methylenedioxyamphetamine (MDA), 3,4-methylenedioxy-methamphetamine (MDMA), 3,4-methylenedioxy-ethylamphetamine (MDEA) and 4-hydroxy-3-methoxymethamphetamine (HMMA).

The clinical diagnostic field has seen a broad expansion in recent years, both as to the variety of materials of interest that may be readily and accurately determined, as well as the methods for the determination. Over the last decade, testing for drugs of abuse has become commonplace. This testing is not only for the monitoring of criminal offenders and drug addicts, but employers also use it for the screening of workers. In recent years, immunoassay based on the reaction of an antibody with an antigen has been extensively investigated for this purpose. Immunoassay may be roughly classified into radioimmunoassay, using a radioactive isotope, enzyme-immunoassay (EIA) using an enzyme and luminescence assays, using fluorescent labels, e.g., fluorescence polarization, and chemiluminescent labels.

Amphetamine and methamphetamine stimulate the central nervous system and have been used medicinally to treat hypotension, narcolepsy and obesity. Because of their stimulating effects, the drugs and derivatives have been abused.

The designer drugs, methylenedioxyamphetamine (MDA), 1-3',4'-methylenedioxyphenyl)-2-propanamine, "Love Pills", methylenedioxy-methamphetamine (MDMA), "Adam", "Ecstasy" and methylenedioxyethylamphetamine (MDEA), "Eve" are entactogens, producing feeling of euphoria and friendliness. These drugs are currently popular and called "rave drugs". It has been demonstrated by several experimental studies on rats and human that these drugs are risky to human. In fact, toxicity and deaths associated with MDMA has been reported. Recent reviews have also reported the hepatotoxicity, neurotoxicity, psychopathology and the abuse potential of these drugs. The common use of these drugs has been widespread in the world and appeared recently as the most popular drug of abuse in certain countries.

Although there is a need for the detection of MDMA, MDA and its metabolites such as 4-hydroxy-3-methoxymethamphetamine (HMMA) and so forth, the literature discloses GC-MS, HPLC detection methods, which are expensive and time consuming. It appears that researchers have tried to use existing amphetamine/methamphetamine immunoassay technology for the detection of MDMA and MDA due to their cross-reactivity. The hope was that the antibody recognizing amphetamine and methamphetamine would also be useful for assays for MDMA, MDA or its metabolites. For instance, three commercial amphetamine/methamphetamine assays, namely, EMIT®, FPIA and RIA, have been investigated for the detection of MDA, MDMA and MDEA. (Ruangyuttikarn, et al., "Comparison of three commercial amphetamine immunoassay for detection of methamphetamine, methylenedioxyamphetamine, methylenedioxy-methamphetamine and methylenedioxyethylamphetamine" J. Anal. Toxicol. 1988, 12, 229; Kunsman, et al., "Application of the Syva Emit and Abbott TDX amphetamine Immunoassays to the detection of 3,4-Methylenedioxy-methamphetamine (MDMA) and 3,4-Methylenedioxyethamphetamine (MDEA) in Urine" J. Anal. Toxicol. 1990, 14, 149; Cody, J. T. "Detection of D,L-amphetamine, D,L-methamphetamine, and illicit amphetamine analogs using diagnostic products corporation's amphetamine and methamphetamine radioimmunoassay" J. Anal. Toxicol. 1990, 14, 321; Ensslin, et al., "Toxicological detection of the designer drug 3,4-methylenedioxyethylamphetamine (MDE, 'Eve') and its metabolites in urine by gas chromatography spectrometry and fluorescence polarization immunoassay" J. Chromatogr. 1996, B683, 189.

However, according to the published literature, the above approaches have achieved little, if any, success. This result is not unexpected due to the very different chemical structures between methamphetamine and MDMA analogs. That is, MDMA and MDA have an extra (methylenedioxy) five-member ring in comparison to methamphetamine and amphetamine, respectively.

There is, therefore, a need for assays for the detection of the aforementioned designer drugs and, in some instances, their major metabolites. The assays should be able to detect the designer drugs in order to monitor and treat patients addicted to these drugs.

SUMMARY OF THE INVENTION

One embodiment of the present invention is a compound of the formula:

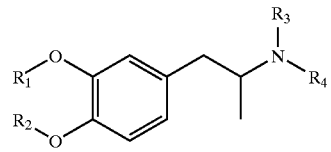

Formula I wherein: $R^1$ is H, lower alkyl, a protecting group, or is taken together with $R^2$ to form a ring, $R^2$ is H, lower alkyl, $-(CH_2)_nSCH_2C(O)R^6$ or $-(CH_2)_n C(SO_2R^6)=CH_2$, or is taken together with $R^1$ to form a ring, $R^3$ and $R^4$ are independently H or lower alkyl or a protecting group, or, when $R^1$ is taken together with $R^2$ to form a ring, at least one of $R^3$ or $R^4$ is $-C(O)(CH_2)_n R^5$, $-C(O)(CH_2)_nNHC(O)R^5$, $-C(O)(CH_2)_nNHC(O)(CH_2)_nSR^5$, $-(CH_2)_nC(SO_2R^5)=CH_2$, $-(CH_2)_n SCH_2C(O)R^5$, or $-(CH_2)_nC(SO_2R^5)=CH_2$, or when $R^1$ is not taken together with $R^2$ to form a ring, at least one of $R^1$ and $R^2$ is not H or lower alkyl or a protecting group, $R^5$ is H, $-OH$, $-SH$, $-O$-lower alkyl, halogen, $NH_2$, -succinimidyl, -maleimidyl, immunogenic carrier, or label, $R^6$ is H, $-OH$, $-SH$, $-O$-lower alkyl, halogen, $NH_2$, -succinimidyl, -maleimidyl, immunogenic carrier, or label, and n is an integer from 1 to 5, and including acid salts thereof.

Another embodiment of the present invention is a compound of the formula:

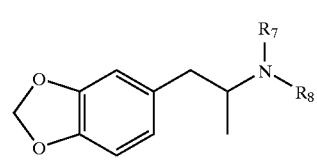

Formula II wherein: $R^7$ is H, lower alkyl, a protecting group, when $R^1$ is taken together with $R^2$ to form a ring, at least one of $R^3$ or $R^4$ is —C(O)(CH$_2$)$_n$R$^5$, —C(O)(CH$_2$)$_n$NHC(O)R$^5$, —C(O)(CH$_2$)$_n$NHC(O)(CH$_2$)$_n$SR$^5$, —(CH$_2$)$_n$C(SO$_2$R$^5$)=CH$_2$, —(CH$_2$)$_n$SCH$_2$C(O)R$^5$, or —(CH$_2$)$_n$C(SO$_2$R$^5$)=CH$_2$, or when $R^1$ is not taken together with $R^2$ to form a ring, at least one of $R^1$ and $R^2$ is not H or lower alkyl or a protecting group, $R^8$ is H, lower alkyl, a protecting group, —C(O)(CH$_2$)$_n$R$^5$, —C(O)(CH$_2$)$_n$NHC(O)R$^5$, —C(O)(CH$_2$)$_n$NHC(O)(CH$_2$)$_n$SR$^5$, —(CH$_2$)$_n$C(SO$_2$R$^5$)=CH$_2$, —(CH$_2$)$_n$SCH$_2$C(O)R$^5$, or —(CH$_2$)$_n$C(SO$_2$R$^5$)=CH$_2$, $R^5$ is H, —OH, —SH, —O-lower alkyl, halogen, NH$_2$, -succinimidyl, -maleimidyl, an immunogenic carrier or label, and n is an integer from 1 to 5, with the proviso that at least one of $R^7$ and $R^8$ are not H or lower alkyl, and including the acid salts thereof.

Another embodiment of the present invention is a compound of the formula:

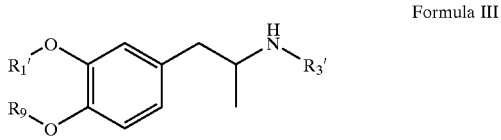

Formula III wherein: $R^{3'}$ is H, methyl or ethyl or a protecting group, $R^{1'}$ is H or lower alkyl or a protecting group, $R^9$ is a protecting group, —(CH$_2$)$_n$SCH$_2$C(O)R$^6$ or —(CH$_2$)$_n$C(SO$_2$R$^6$)=CH$_2$, $R^6$ is H, —OH, —SH, —O-lower alkyl, halogen, NH$_2$, an immunogenic carrier, -succinimidyl, -maleimidyl, or label, and n is an integer from 1 to 5, and including acid salts thereof.

Another embodiment of the present invention is a method for determining a compound selected from the group consisting of 3,4-methylenedioxyamphetamine (MDA), 3,4-methylenedioxy-methamphetamine (MDMA), 3,4-methylenedioxy-ethylamphetamine (MDEA) and 4-hydroxy-3-methoxy-methamphetamine (HMMA). The method comprises providing in combination in a medium (i) a sample suspected of containing the compound and (ii) an antibody raised against a compound of Formula I, Formula II or Formula III that comprises a protein. The medium is examined for the presence a complex comprising the compound and the antibody where the presence of such as complex indicates the presence of the compound in the sample. In one aspect of the above embodiment, the combination further comprises a label conjugate of the above compound.

Another embodiment of the present invention is a kit for determining a compound selected from the group consisting of 3,4-methylenedioxyamphetamine (MDA), 3,4-methylenedioxy-methamphetamine (MDMA), 3,4-methylenedioxy-ethylamphetamine (MDEA) and 4-hydroxy-3-methoxy-methamphetamine (HMMA). The kit comprises (a) an antibody raised against a compound of Formula I, Formula II or Formula III that comprises a protein and (b) ancillary reagents for determining the compound. The kit may further comprise (c) a label conjugate of the compound of the above formula.

BRIEF DESCRIPTION OF THE DRAWINGS

FIG. 1 is a reaction scheme depicting an example of a synthesis of MDMA-KLH immunogen (10).

FIG. 2 is a reaction scheme depicting an example of a synthesis of MDA-KLH immunogen (14).

FIG. 3 is a reaction scheme depicting an example of a synthesis of MDMA haptens (15)–(17).

FIG. 4A is a reaction scheme depicting an example of a synthesis of MDA haptens (18)–(19).

FIG. 4B is a reaction scheme depicting an example of a synthesis of MDA hapten (20).

FIG. 5 is a reaction scheme depicting an example of a synthesis of HMMA intermediate (29) for immunogen (30).

FIG. 6 is a reaction scheme depicting an example of a synthesis of HMMA-KLH immunogen (30).

FIG. 7 is a reaction scheme depicting an example of a synthesis of HMMA-KLH immunogen (36).

FIG. 8A is a reaction scheme depicting an example of a synthesis of MDMA hapten (38).

FIG. 8B is a reaction scheme depicting an example of a synthesis of MDMA hapten intermediate (40).

DESCRIPTION OF THE SPECIFIC EMBODIMENTS

Figure 9:
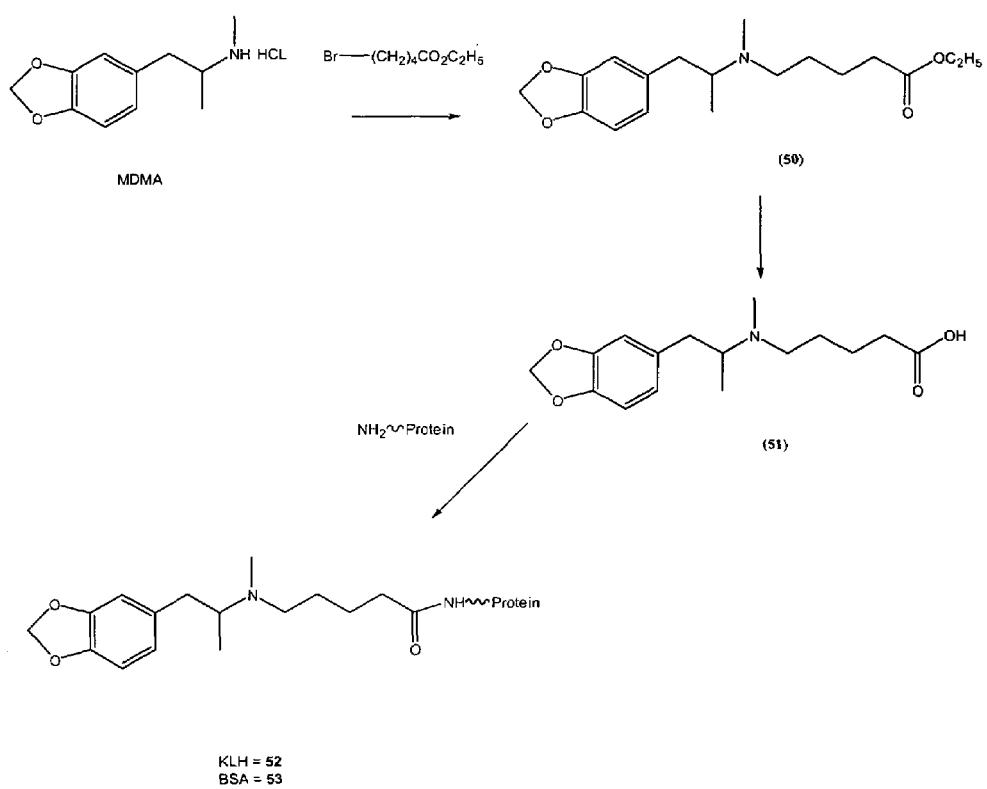
FIG. 9 is a reaction scheme depicting an example of a synthesis of MDMA-KLH immunogen (52) or MDMA-BSA immunogen (53).

Immunogens comprising proteins are synthesized and used to prepare antibodies specific for 3,4-methylenedioxyamphetamine (MDA), 3,4-methylenedioxy-methamphetamine (MDMA), 3,4-methylenedioxy-ethylamphetamine (MDEA) and 4-hydroxy-3-methoxymethamphetamine (HMMA). The antibodies may be used in methods for detecting the aforementioned drugs in samples suspected of containing the drugs. Label conjugates are prepared and may be employed in the above methods. Effective screening of samples for the presence of one or more entactogens as referred to above may be realized.

The immunogens and label conjugates may involve an analog of MDA, MDMA, MDEA or HMMA linked through the nitrogen, or in the case of HMMA alternatively through the 4-position of the benzene ring, to a protein or a label, respectively. The linking group may comprise about 2 to about 10 atoms not counting hydrogen and may comprise a chain of from 2 to 8 atoms, each independently selected from the group normally consisting of carbon, oxygen, sulfur, nitrogen, halogen and phosphorous. Where the linking group provides attachment of a protein to the 4-position of the benzene ring of HMMA, the linking group usually comprises at least 5 atoms or, when less than 5 atoms, the linking group does not comprise solely carbon or oxygen.

The number of heteroatoms in the linking groups will normally range from about 0 to 6, usually from about 1 to 5. The linking groups may be aliphatic or aromatic. When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group has a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities will be linked to amine groups, carboxyl groups, active olefins, alkylating agents, e.g., bromoacetyl. Where an amine and carboxylic acid or its nitrogen derivative or phosphoric acid is linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed. Various linking groups are well known in the art; see, for example, Cautrecasas, *J. Biol. Chem.* (1970) 245:3059.

As mentioned above, one aspect concerns compounds of the formula:

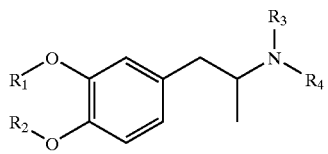

wherein: $R^1$ is H, lower alkyl, a protecting group, or is taken together with $R^2$ to form a ring, which may be a five- or six-member ring, usually a five-member ring;

$R^2$ is H, lower alkyl, a protecting group, —$(CH_2)_nC(O)R^6$, —$(CH_2)_nSCH_2C(O)R^6$, —$(CH_2)_nR^6$, or —$(CH_2)_nC(SO_2R^6)=CH_2$, or is taken together with $R^1$ to form a ring as discussed above, preferably, $R^2$ is H, lower alkyl, —$(CH_2)_nSCH_2C(O)R^6$ or —$(CH_2)_nC(SO_2R^6)=CH_2$, or taken together with $R^1$ to form a ring, $R^3$ and $R^4$ are independently H or lower alkyl or a protecting group, or, when $R^1$ is taken together with $R^2$ to form a ring, at least one of $R^3$ or $R^4$ is —$C(O)(CH_2)_nR^5$, —$C(O)(CH_2)_nNHC(O)R^5$, —$C(O)(CH_2)_nNHC(O)(CH_2)_nSR^5$, —$(CH_2)_nC(SO_2R^5)=CH_2$, —$(CH_2)_nSCH_2C(O)R^5$, or —$(CH_2)_nC(SO_2R^5)=CH_2$, or when $R^1$ is not taken together with $R^2$ to form a ring, at least one of $R^1$ and $R^2$ is not H or lower alkyl, preferably, $R^3$ and $R^4$ are independently H or lower alkyl or a protecting group, or, when $R^1$ is taken together with $R^2$ to form a ring, at least one, preferably, one, of $R^3$ or $R^4$ is —$C(O)(CH_2)_nR^5$, —$C(O)(CH_2)_nNHC(O)R^5$, —$C(O)(CH_2)_nNHC(O)(CH_2)_nSR^5$, —$(CH_2)_nC(SO_2R^5)$ =$CH_2$, —$(CH_2)_nSCH_2C(O)R^5$, or —$(CH_2)_nC(SO_2R^5)$ =$CH_2$, or when $R^1$ is not taken together with $R^2$ to form a ring, $R^2$ is —$(CH_2)_nSCH_2C(O)R^6$ or —$(CH_2)_n C(SO_2R^6)=CH_2$, $R^5$ is H, —OH, —SH, —O-lower alkyl, halogen (bromine, chlorine, iodine, fluorine, usually, bromine or chlorine), —$NH_2$, -succinimidyl, -maleimidyl, immunogenic carrier, or label, $R^6$ is H, —OH, —SH, —O-lower alkyl, halogen, $NH_2$, -succinimidyl, -maleimidyl, immunogenic carrier, or label, and n is an integer from 1 to 5, 1 to 4, 1 to 3, 1 to 2, or 1; with the proviso that, when $R^1$ is $CH_3$, $R^2$ is not —$CH_2C(O)R^6$, and with the proviso that, when $R^1$ is taken together with $R^2$ to form a ring and when only one of $R^3$ and $R^4$ is H or lower alkyl and the other of $R^3$ and $R^4$ is —$(CH_2)_nC(O)R^5$, $R^5$ is a protein, and including acid salts thereof.

By the term "lower alkyl" is meant a branched or unbranched saturated monovalent hydrocarbon radical containing 1 to 10, usually, 1 to 5, carbon atoms, such as methyl, ethyl, propyl, butyl and pentyl, and including the normal, secondary, tertiary, and the like, forms thereof where appropriate.

By the term "acid salts thereof" is meant salts formed with acids such as mineral acids, for example, hydrochloric acid, and the like, organic acids, for example, trifluoroacetic acid and the like.

By "-succinimidyl" is meant the following:

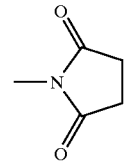

By "-maleimidyl" is meant the following:

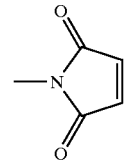

By the term "label" is meant a member of a signal producing system. The label is capable of being detected directly or is detectable through a specific binding reaction that produces a detectable signal. The labels generally are radioisotopic, luminescent, particulate or enzymic. The label can be a poly(amino acid), or protein, or non-poly(amino acid), isotopic or non-isotopic, usually non-isotopic, and can be a catalyst, such as an enzyme, a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The term "non-poly(amino acid) labels" refers to those labels that are not proteins such as enzymes. A non-poly (amino acid) label may be a member of a signal producing system. The non-poly(amino acid) label is capable of being detected directly or is detectable through a specific binding reaction that produces a detectable signal. The non-poly (amino acid) labels generally are radioisotopic, luminescent, particulate, polynucleotidic or the like. More particularly, the label can be isotopic or non-isotopic, usually non-isotopic, and can be a polynucleotide coding for a catalyst, promoter, dye, fluorescent molecule, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like.

The signal producing system may have one or more components, at least one component being the label. The signal producing system generates a signal that relates to the presence of an entactogen in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Exemplary signal-producing systems are described in U.S. Pat. No. 5,508, 178 (Rose, et al.), the relevant disclosure of which is incorporated herein by reference.

By the term "immunogenic carrier" is meant a group which, when conjugated to a hapten and injected into a mammal, will induce an immune response and elicit the production of antibodies that bind to the hapten. Haptens are compounds capable of binding specifically to corresponding antibodies, but do not themselves act as immunogens (or antigens) for preparation of the antibodies. Antibodies that recognize a hapten can be prepared against compounds comprised of the hapten linked to an immunogenic (or antigenic) carrier. Immunogenic carriers are also referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, incorporated herein by reference. Immunogenic carriers include proteins such as, for example, albumins, serum proteins, e.g., globulins, ocular lens proteins and lipoproteins, and so forth. Illustrative proteins include bovine serum albumin (BSA), keyhole limpet hemocyanin ("KLH"), egg ovalbumin, bovine gamma-globulin (BGG) and the like.

Included within the above compounds are compounds of the formula:

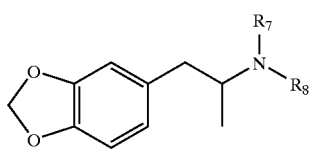

wherein: $R^7$ is H, lower alkyl, a protecting group, —$(CH_2)_n$C(O)$R^5$, —C(O)$(CH_2)_n R^5$, —C(O)$(CH_2)_n$NHC(O)$R^5$, —$(CH_2)_n$C($SO_2 R^5$)=$CH_2$, —$(CH_2)_n$$SCH_2$C(O)$R^5$, —C(O)$(CH_2)_n$NHC(O)$(CH_2)_n$$SR^5$, —$(CH_2)_n R^5$, or —$(CH_2)_n$C($SO_2 R^5$)=$CH_2$, preferably, $R^7$ is H, lower alkyl, a protecting group, —C(O)$(CH_2)_n R^5$, —C(O)$(CH_2)_n$NHC(O)$R^5$, —C(O)$(CH_2)_n$NHC(O)$(CH_2)_n$$SR^5$, —$(CH_2)_n$C($SO_2 R^5$)=$CH_2$, —$(CH_2)_n$$SCH_2$C(O)$R^5$, or —$(CH_2)_n$C($SO_2 R^5$)=$CH_2$, $R^8$ is H, lower alkyl, a protecting group, —$(CH_2)_n$C(O)$R^5$, —C(O)$(CH_2)_n R^5$, —C(O)$(CH_2)_n$NHC(O)$R^5$, —$(CH_2)_n$C($SO_2 R^5$)=$CH_2$, —$(CH_2)_n$$SCH_2$C(O)$R^5$, —C(O)$(CH_2)_n$NHC(O)$(CH_2)_n$$SR^5$, —$(CH_2)_n R^5$, or —$(CH_2)_n$C($SO_2 R^5$)=$CH_2$, preferably, $R^8$ is H, lower alkyl, a protecting group, —C(O)$(CH_2)_n R^5$, —C(O)$(CH_2)_n$NHC(O)$R^5$, —C(O)$(CH_2)_n$NHC(O)$(CH_2)_n$$SR^5$, —$(CH_2)_n$($SO_2 R^5$)=$CH_2$, —$(CH_2)_n$$SCH_2$C(O)$R^5$, or —$(CH_2)_n$C($SO_2 R^5$)=$CH_2$, $R^5$ is H, —OH, —SH, —O-lower alkyl, halogen, $NH_2$, —NH-protein where the protein is a label or an immunogen, -succinimidyl, -maleimidyl, or non-poly(amino acid) label, or non-poly(amino acid) immunogenic carrier, and n is an integer from 1 to 5, 1 to 4, 1 to 3, 1 to 2, or 1, with the proviso that at least one of $R^7$ and $R^8$ are not H or lower alkyl, and with the proviso that, when only one of $R^7$ and $R^8$ is H or lower alkyl and the other of $R^7$ and $R^8$ is —$(CH_2)_n$C(O)$R^5$, $R^5$ is a protein, and including the acid salts thereof.

Also included within the above compounds are compounds of the formula:

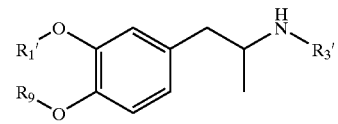

wherein: $R^{3'}$ is H, methyl or ethyl or a protecting group,
$R^{1'}$ is H or lower alkyl such as, for example, methyl, ethyl, and so forth, or a protecting group,
$R^9$ is a protecting group, —$(CH_2)_n$$SCH_2$C(O)$R^6$, —$(CH_2)_n R^6$, or —$(CH_2)_n$C($SO_2 R^6$)=$CH_2$, preferably, $R^9$ is a protecting group, —$(CH_2)_n$$SCH_2$C(O)$R^6$ or —$(CH_2)_n$C($SO_2 R^6$)=$CH_2$,
$R^6$ is H, —OH, —SH, —O-lower alkyl, halogen, $NH_2$, —NH-protein where the protein is a label or an immunogen, -succinimidyl, -maleimidyl, or non-poly(amino acid) label, or non-poly(amino acid) immunogenic carrier, and
n is an integer from 1 to 5, 1 to 4, 1 to 3, 1 to 2, or 1, and including acid salts thereof.

Also included within the above are compounds of the formula:

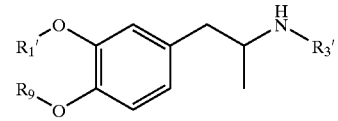

wherein: $R^{3'}$ is methyl or ethyl,
$R^{1'}$ is lower alkyl,
$R^9$ is —$(CH_2)_nSCH_2C(O)R^6$, —$(CH_2)_nR^6$, or —$(CH_2)_nC(SO_2R^6)$=$CH_2$,
$R^6$ is H, —OH, —SH, —O-lower alkyl, halogen, $NH_2$, —NH-protein where the protein is a label or an immunogen, -succinimidyl, -maleimidyl, or non-poly(amino acid) label, or non-poly(amino acid) immunogenic carrier, and
n is an integer from 1 to 5,
and including acid salts thereof.
Another embodiment is a compound of the formula:

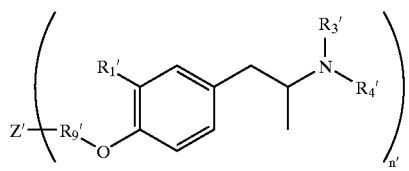

wherein:
$R^{1'}$ is H, lower alkyl, or a protecting group, preferably, H,
$R^{3'}$ is H, lower alkyl, e.g., methyl, ethyl, etc., or a protecting group,
$R^{4'}$ is H, lower alkyl, or a protecting group,
$R^{9'}$ is —$(CH_2)_nSCH_2C(O)R^{6'}$, —$(CH_2)_nR^{6'}$, or —$(CH_2)_nC(SO_2R^{6'})$=$CH_2$,
$R^{6'}$ is Z', which is an enzyme,
n' is an integer between 1 and the molecular weight of said enzyme divided by about 500.
Another embodiment is a compound of the formula:

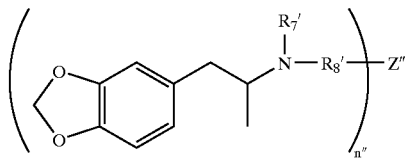

wherein:
$R^{7'}$ is H, lower alkyl, or a protecting group,
$R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$,
$R^{5'}$ is Z", which is an enzyme,
n" is an integer between 1 and the molecular weight of said enzyme divided by about 500.
Another embodiment is a compound of the formula:

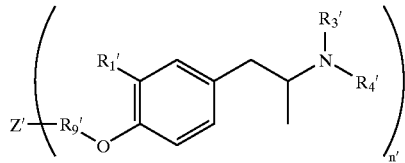

wherein:
$R^{1'}$ is H, methyl, ethyl, or a protecting group, preferably, H,
$R^{3'}$ is H, lower alkyl, or a protecting group,
$R^{4'}$ is H, lower alkyl, or a protecting group,
$R^{9'}$ is —$(CH_2)_nSCH_2C(O)R^{6'}$, —$(CH_2)_nR^{6'}$, or —$(CH_2)_nC(SO_2R^{6'})$=$CH_2$, preferably, $R^{9'}$ is —$(CH_2)_nSCH_2C(O)R^{6'}$ or —$(CH_2)_nC(SO_2R^{6'})$=$CH_2$,
$R^{6'}$ is Z', which is an immunogenic protein or a non-poly(amino acid) immunogenic carrier,
n' is an integer between 1 and the molecular weight of said immunogenic protein or said immunogenic carrier divided by about 500.
Another embodiment is a compound of the formula:

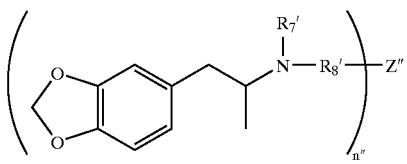

wherein:
$R^{7'}$ is H, lower alkyl, or a protecting group,
$R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$,
$R^{5'}$ is Z", which is an immunogenic protein or a non-poly(amino acid) immunogenic carrier,
n" is an integer between 1 and the molecular weight of said immunogenic protein or said immunogenic carrier divided by about 500.

Synthesis

The synthesis of representative examples of the above compounds is discussed herein by way of illustration and not limitation. Other synthetic procedures will be suggested to those skilled in the art in view of the disclosure herein. Other compounds within the scope of the present invention may be prepared using suitable variants of the reagents employed below.

MDMA-KLH immunogen (10) may be synthesized by a procedure outlined in FIG. 1. MDMA (1) is reacted with methyl bromoacetate in the presence of a base to give compound 7. Suitable bases include metal hydrides such as, e.g., NaH, $CaH_2$, etc. sodium carbonate, potassium carbonate, and the like, in an organic solvent such as, for example, dimethylformamide (DMF), organic ethers, e.g., ethyl ether, tetrahydrofuran (THF), dioxane, and the like. Hydrolysis of compound 7 may be achieved in an aqueous organic medium in the presence of a base such as, e.g., ammonium hydroxide in an alcohol such as methanol, ethanol, and the like, potassium, sodium carbonate, sodium hydroxide, and the like, in aqueous methanol, ethanol, and so forth. After hydrolysis, the pH of the medium is lowered to about 3 to about 4 by addition of an acid such as a mineral acid or an organic acid such as, for example, acetic acid, hydrochloric acid and the like. The resulting acid 8 is reacted to form an activated intermediate, usually an activated ester. In one exemplary approach, acid 8 is treated with 1-ethyl-3-(3-dimethylaminopropyl)carbodiimide hydrochloride (EDAC)

and N-hydroxysuccinimide (NHS) to yield the desired activated ester intermediate 9. Reaction of intermediate 9 with a protein such as KLH in a buffer solution such as a phosphate buffer, e.g., sodium phosphate (0.1 M, pH=8.0), gives the desired immunogen 10. The latter compound may be purified by known techniques such as, for example, dialysis, chromatography, and combinations thereof. The attachment of a protein to the linking moiety of the molecule is usually by way of amino groups on a protein, where the nitrogen of the amino group may be considered the nitrogen of a linking group.

An exemplary synthesis of MDA-KLH immunogen 14 is depicted in FIG. 2. The synthesis is carried out in a manner similar to that described above for the synthesis of compound 10.

The following discussion relates to the syntheses of MDMA haptens for subsequent reaction to form protein immunogenic conjugates. The starting compound in each of the reaction schemes shown in FIG. 3 is MDMA (1). The reaction temperatures are about ambient temperature, i.e., about 25° C. For the preparation of compound 15, MDMA (1) is reacted with an activated ester of bromoacetic acid, namely, the N-hydroxy succinimide ester of bromoacetic acid in this example, under basic conditions, which include incorporating into the reaction mixture an alkyl amine such as, for example, diisopropylethylamine, ethylamine, triethylamine and the like. The reaction is conducted in an organic solvent such as, for example, an ether, e.g., THF, ethyl ether and so forth. For the preparation of compound 16, MDMA (1) is reacted with an activated ester of bromoacetylglycine, namely, the N-hydroxy succinimide ester in the example shown in FIG. 3. The reaction is carried out under basis conditions with an organic solvent as discussed above for the preparation of compound 15. For the preparation of vinyl sulfone 17, MDMA (1) is reacted with an activated compound, namely, in the example shown, a double-activated reagent, i.e., 1,3-dibromo-2-(methylsulfonyl)propane. The double-activated reagent reacts with the amine moiety of MDMA in the presence of a base such as, for example, a metal hydride, e.g., sodium hydride, calcium hydride, a carbonate, e.g., potassium carbonate, sodium carbonate and the like.

Similar chemistry may be applied to the preparation of MDA haptens as shown in FIGS. 4A and 4B. For the preparation of compound 18, MDA (4) is reacted with an activated ester of bromoacetic acid, for instance, the N-hydroxy succinimide ester of bromoacetic acid in this example, under basic conditions, as discussed above for the preparation of compound 15. For the preparation of compound 19, MDA (4) is reacted with an activated ester of bromoacetylglycine, namely, the N-hydroxy succinimide ester in the example shown in FIG. 4A. The reaction is carried out under basis conditions with an organic solvent as discussed above for the preparation of compound 16. For the preparation of vinyl sulfone 20 (FIG. 4B), MDA (4) is reacted with an activated compound, namely, in the example shown, a double-activated reagent, i.e., 1,3-dibromo-2-(methylsulfonyl)propane. The double-activated reagent reacts with the amine moiety of MDMA under basic conditions as discussed above for the preparation of compound 17. Besides the preferred monoalkylation product 20, a dialkylation product 21, which has two vinyl sulfone moieties on the nitrogen atom, is obtained. To achieve monoalkylation the reaction is carried out at lower temperature such as, for example, about −10° C. to about −50° C., usually, about −20° C. to about −30° C. and a controlled amount of the double-activated reagent is employed, namely, an approximate reagent ratio of about 1 to about 1. In this way, monoalkylation product may be exclusively obtained in yields that are 80% or greater.

An exemplary synthesis of a HMMA immunogen is depicted in FIG. 5 and FIG. 6. Referring to FIG. 5, Ketone 22 is subjected to reductive amination in a two-step process. In the first step, ketone 22 is reacted, for example, with methylamine hydrochloride under basic conditions. Generally, a buffered aqueous medium containing an organic solvent, for instance, an alcohol, e.g., methanol or the like, is employed. This step yields intermediate compound 23, which is treated with a reducing agent such as a metal hydride, for example, $NaBH_3CN$ in an organic solvent such as an alcohol, e.g., methanol, and the like. The aqueous medium may contain a carbonate buffer such as sodium carbonate, potassium carbonate, and the like. Compound 24 is obtained and treated to protect the amine functionality, thus yielding compound 25. Suitable protecting groups are well known in the art and have been described in detail in numerous patents and articles in the technical literature. See, for example, "Principles of Peptide Synthesis" (M. Bodanszky, Springer Verlag, Berlin, Heidelberg, New York, Tokyo (1984). Examples of such protecting groups, by way of example and not limitation, are t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentyl-ethoxycarbonyl, bromobenzyloxy, carbamyl, formyl, and the like. The particular protecting group chosen depends on the nature of the reaction to be performed and the conditions of such reaction such as temperature, pH, and so forth.

Referring again to FIG. 5, the protecting group employed in this exemplary synthesis is di-tert-butyldicarbonate $((tBoc)_2O)$ in an aqueous organic solvent such as an ether, e.g., THF and the like. A suitable carbonate such as potassium carbonate, sodium carbonate, and the like, is included in the reaction medium to provide for basic conditions. Reaction of 25 with methyl bromoacetate in the presence of a metal hydride, e.g., NaH, in an organic solvent, e.g., DMF, yields compound 26. The protecting group is removed under acidic conditions in an organic solvent to give compound 27. In the example depicted, compound 26 is treated with trifluoroacetic acid (TFA) in methylene chloride. In general, removal of the protecting group is dependent on the nature of the protecting group. Suitable conditions for removal of protecting groups are well known in the art. Compound 27 is treated to convert it to the hydrochloric acid salt compound 28. Exemplary conditions involve hydrolysis under basic conditions such as, e.g., a carbonate such as potassium carbonate in an organic solvent such as methanol. Subsequently, hydrochloric acid is added to form the hydrochloric acid salt. Compound 28 is treated to form activated ester compound 29. Exemplary conditions include, e.g., reacting with EDAC and NHS. Referring to FIG. 6, immunogen 30 is obtained by reaction of compound 29 with a protein, e.g., KLH and the like, in a suitable buffer of pH about 7.5 to about 9.0, preferably, about 8, such as, e.g., a phosphate buffer, e.g., sodium phosphate (0.1 M, pH=8.0) and the like. Immunogen 30 may be purified as discussed above.

The synthesis of other immunogens of HMMA may be achieved (FIG. 7) by using common intermediate compound 25. Alkylation of the phenolic group of compound 25 may be achieved using a suitable di-activated alkane such as, for example, dibromoethane and so forth under basic conditions such as, for example, a carbonate, e.g., potassium carbonate and the like, in an organic solvent such as an aromatic compound, e.g., toluene and the like. The product of the above reaction, namely, compound 31 is treated with a thioester salt of an organic acid such as, for example, potassium thioacetate, potassium thiopropanoate and the like, in an aqueous organic solvent such as methanol water and so forth. The resulting compound 32 is then treated to remove the protecting group and hydrolyze the acetate, in a manner similar to that described above, to obtain thiol compound 34. Bromoacetyl-KLH 35 is obtained by reaction of KLH with an activated ester of bromoacetic acid, namely, the N-hydroxy succinimide ester of bromoacetic acid in this example, under basic conditions, as discussed above for the preparation of compound 15. Reaction of thiol 34 with bromoacetyl-KLH 35 yields immunogenic compound 36, which may be purified as discussed above.

The synthesis of HMMA vinyl sulfone hapten 38 is set forth in FIG. 8.

Reaction of compound 25 with 1,3-dibromo-2-(methylsulfonyl)propane under basic condition gives compound 37. The reactions are similar to those described above for the syntheses of FIG. 4. Hapten 38 is obtained by removal of the protecting group as discussed above.

Referring again to FIG. 8, alkylation of phenol 25 with, for example, bromoacetonitrile, under basic conditions such as, e.g., a carbonate in an organic solvent, gives intermediate compound 39. The basic conditions are similar to those described above. In the example depicted, potassium carbonate in DMF is employed at elevated temperature, e.g., about 80° C. Reduction of 39 with a metal hydride such as, e.g., $NaBH_4$ and the like, in the presence of a Group VIII metal halide (chloride, bromide, fluoride and iodide) such as, for example, $CoCl_2$, $FeCl_2$ and so forth, yields amine 40, which may be employed to synthesize a hapten and also an immunogen by reaction with an immunogenic carrier.

Referring to FIG. 9, synthesis of compound 51 commences with the reaction of MDMA hydrochloride with ethyl 5-bromo valerate under basic conditions to give compound 50. The basic conditions include, for example, an inorganic base, e.g., a carbonate, e.g., potassium carbonate, sodium carbonate, and the like in an organic solvent such as, for example, a formamide, e.g., dimethylformamide (DMF), and so forth. Hydrolysis of 50 gave acid 51. Hydrolysis may be carried out, for example, using an inorganic base such as, for example, a metal hydroxide, e.g., sodium hydroxide, potassium hydroxide, and the like in an oxygenated organic solvent such as, for example, an alcohol, e.g., methanol, ethanol, and so forth. Acid 51 is attached to a protein giving KLH (52) and BSA (53) immunogens. Acid 51 was activated by DCC and NHS ester and followed a reaction with amine either from KLH or BSA to give immunogens 52 and 53, respectively.

The assays of the present invention usually involve reactions between binding partners such as an entactogen analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding-pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

The immunogens prepared in accordance with the present invention may be employed to prepare antibodies specific for a respective entactogen mentioned above. An antibody is an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector, which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth.

An analyte analog is a modified analyte, which can compete with the analogous analyte for a receptor, the modification providing means to join an analyte analog to another molecule. The analyte analog will usually differ from the analyte by more than replacement of a hydrogen with a bond that links the analyte analog to a hub or label, but need not. The analyte analog can bind to the receptor in a manner similar to the analyte. The analog may be, for example, a label conjugate of the analyte, an antibody directed against the idiotype of an antibody to the analyte and the like.

As indicated above, analyte analogs include label conjugates, which may be prepared from certain of the haptens described above by incorporation of a desired label. The two components may be bound together, optionally through a linking group, to form a single structure. The binding can be either covalent attachment such as by a direct connection, e.g., a chemical bond, between the components or between the components and a linking group or non-covalent attachment involving specific binding between complementary specific binding pair (sbp) members that are attached to components. The procedures employed for the conjugation are well-known in the art.

Typically, for covalent attachment, one or more of the components contains a functional group suitable for attachment to one or more of the other components. The functional groups suitable for attaching the components may be carbonyl functionalities, both oxocarbonyl, e.g., aldehyde, and non-oxocarbonyl (including nitrogen and sulfur analogs) e.g., carboxy, amidine, amidate, thiocarboxy and thionocarboxy. Alternative functionalities of oxo include active halogen, diazo, mercapto, olefin, particularly activated olefin, amino, phosphoro and the like. Of particular interest are activated esters or alkylating agents. Details of techniques for attaching molecules to one another are well known in the art. See, for example, Matthews, et al., *Anal. Biochem.* (1985) 151:205–209; Engelhardt, et al., European Patent Application No. 0302175 and U.S. Pat. No. 3,817,837, the relevant disclosure of which is incorporated herein by reference in its entirety.

As indicated above, the components, i.e., hapten and label, of the reagents may be attached together non-covalently. For example, a small organic molecule such as, for example, biotin including bis-biotin, fluorescein or the like may be incorporated into one of the components and the other component may be linked to a binding partner for the small organic molecule such as, for example, respectively, streptavidin, anti-fluorescein or the like. The binding of the binding partners results in the non-covalent attachment of the components to one another.

Assays

The aforementioned reagents may be employed in all types of immunoassays to determine the presence and/or amount of entactogen analytes in a sample suspected of containing such analytes. The immunoassays may involve labeled or non-labeled reagents. Immunoassays involving non-labeled reagents usually comprise the formation of relatively large antigen-antibody complexes. Such assays include, for example, immunoprecipitin and agglutination methods and corresponding light scattering techniques such as, e.g., nephelometry and turbidimetry, for the detection of antigen-antibody complexes. Labeled immunoassays include enzyme immunoassays, fluorescence polarization immunoassays, radioimmunoassay, inhibition assay, luminescent oxygen channeling assay, and so forth.

One general group of immunoassays includes immunoassays of antigens or haptens using labeled analyte with a limited concentration of antibody. Another group of immunoassays involves the use of an excess of all of the principal reagents. Such assays include two-site sandwich assays, e.g., immunoradiometric assays, immunofluorometric assays, immunochemiluminometric assays, ELISA assays, and so forth. Another group of immunoassays includes precipitation, nephelometric and turbidimetric immunoassays, particle agglutination immunoassays, particle counting immunoassays, and the like. Another group of immunoassays are separation-free homogeneous assays in which the labeled reagents modulate the label signal upon antigen-antibody binding reactions. Another group of assays includes labeled antibody reagent limited competitive assays for hapten or antigen that avoid the use of problematic labeled antigens or haptens. In this type of assay, it is important that the solid phase immobilized analyte be present in a constant, limited amount. The partition of a label between the immobilized analyte and free analyte depends on the concentration of analyte in the sample.

The aforementioned haptens, label conjugates and antibodies may be employed to conduct an immunoassay for the entactogen analytes MDA, MDMA, HMMA and/or MDEA. The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354, 693; and so forth.

Other enzyme immunoassays are the enzyme modulate mediated immunoassay ("EMMIA") discussed by Ngo and Lenhoff, FEBS Lett. (1980) 116:285–288; the substrate labeled fluorescence immunoassay ("SLFIA") disclosed by Oellerich, J. Clin. Chem. Clin. Biochem. (1984) 22:895–904; the combined enzyme donor immunoassays ("CEDIA") disclosed by Khanna, et al., Clin. Chem. Acta (1989) 185:231–240; homogeneous particle labeled immunoassays such as particle enhanced turbidimetric inhibition immunoassays ("PETINIA"), particle enhanced turbidimetric immunoassay ("PETIA"), etc.; and the like.

Exemplary of heterogeneous assays are the enzyme linked immunosorbant assay ("ELISA") discussed in Maggio, E. T. supra; the radioimmunoassay, disclosed in Yalow, et al., J. Clin. Invest. 39:1157 (1960) and so forth.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of an antigen or hapten. Such assays include, for example, optical immunosensor assays, acoustic immunosensor assays, semiconductor immunosensor assays, electrochemical transducer immunosensor assays, potentiometric immunosensor assays, amperometric electrode assays, and the like.

The above reagents may also be employed in multi-analyte immunoassays where one or more entactogen analytes may be the subject of detection along with one or more other analytes such as other drugs of abuse and the like. Such multi-analyte systems are described in U.S. Pat. No. 5,135,836, the relevant portions of which are incorporated herein by reference.

The homogeneous or heterogeneous assays, particularly enzyme immunoassays and fluorescence polarization immunoassays, are normally carried out in an aqueous buffered medium at a moderate pH, generally that which provides optimum assay sensitivity. The aqueous medium may be solely water or may include from 0 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the method in accordance with the present invention. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° to about 99° C., usually from about 15° C. to about 70° C., more usually 20° C. to about 45° C. The time period for the incubation is about 0.2 seconds to about 6 hours, usually, from about 2 seconds to about 1 hour, more usually, about 1 to about 5 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., more usually from about 15 to about 40° C.

The concentration of entactogen analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte will normally determine the concentrations of the various reagents.

The concentration of analytes to be detected will generally vary from about $10^{-5}$ to about $10^{-17}$ M, more usually from about $10^{-6}$ to about $10^{-14}$ M. In general, a predetermined cut-off level is established for each analyte suspected of being in a sample. The particular predetermined cut-off level generally is determined on an analyte by analyte basis. Those skilled in the art are well aware of the factors relating to the selection of predetermined cut-off levels. For example, for many drugs of abuse, the cut-off levels are determined by SAMSA, an agency of the Department of Health and Human Services. The nature of the signal producing system may be a consideration in determining the predetermined cut-off levels of some analytes. Another consideration is that the expected variation in concentration of the analytes that is of significance should provide an accurately measurable signal difference.

The concentrations of the various reagents in the assay medium will generally be determined by the concentration range of interest of the entactogen analyte. However, the final concentration of each of the reagents will normally be determined empirically to optimize the sensitivity of the assay over the range. That is, a variation in concentration of entactogen analyte that is of significance should provide an accurately measurable signal difference. Considerations such as the nature of the signal producing system and the nature of, and predetermined cut-off levels for, the entactogen analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition, generally ranging from about 30 seconds to about 6 hours, more usually from about 1 minute to about 1 hour.

The following examples further describe the specific embodiments of the invention by way of illustration and not limitation and are intended to describe and not to limit the scope of the invention.

In a homogeneous assay after all of the reagents have been combined, the signal is determined and related to the amount of entactogen analyte in the sample. For example, in an EMIT assay for MDA, a sample suspected of containing MDA is combined in an aqueous medium either simultaneously or sequentially with an MDA-enzyme conjugate and antibody capable of recognizing MDA and the conjugate, both of which are prepared in accordance with the present invention. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The MDA and the MDA-enzyme conjugate compete for binding sites on the antibody. The enzyme activity in the medium is then determined, usually by spectrophotometric means, and is compared to the enzyme activity determined when calibrators or reference samples are tested in which a known amount of MDA is present. Typically, the calibrators are tested in a manner similar to the testing of the sample suspected of containing MDA. The calibrators will typically contain differing, but known, concentrations of the MDA analyte to be determined. Preferably, the concentration ranges present in the calibrators will span the range of suspected MDA concentrations in the unknown samples.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In a typical competitive assay a support having an antibody for an entactogen analyte such as, for example, an antibody for MDA, bound thereto is contacted with a medium containing the sample and an MDA-label conjugate where MDA is conjugated to a detectable label such as an enzyme. After separating the support and the medium, the label activity of the support or the medium is determined by conventional techniques and related to the amount of MDA in the sample.

The support may be comprised of an organic or inorganic, solid or fluid, water insoluble material, which may be transparent or partially transparent. The support can have any of a number of shapes, such as particle, including bead, film, membrane, tube, well, strip, rod, plate and the like. Depending on the type of assay, the support may or may not be suspendable in the medium in which it is employed. Examples of suspendable supports are polymeric materials such as latex, lipid bilayers or liposomes, oil droplets, cells and hydrogels. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials.

Binding of components to the surface of a support may be direct or indirect, covalent or non-covalent and can be accomplished by well-known techniques, commonly available in the literature, as discussed above. See, for example, "Immobilized Enzymes," Ichiro Chibata, Halsted Press, New York (1978) and Cautrecasas, *J. Biol. Chem.*, 245:3059 (1970). The surface of the support is usually polyfunctional or is capable of being polyfunctionalized or is capable of binding to an sbp member, or the like, through covalent or specific or non-specific non-covalent interactions. Such binding is indirect where non-covalent interactions are used and is direct where covalent interactions are employed. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above).

Binding of the antibody for MDA and MDA results in the formation of an immune complex that can be detected directly or indirectly in numerous ways that are well known in the art. The immune complexes are detected directly, for example, when the antibodies employed are conjugated to a label. The immune complex is detected indirectly by examining for the effect of immune complex formation in an assay medium on a signal producing system or by employing a labeled receptor that specifically binds to an antibody produced by employing one of the hapten immunogen conjugates of the invention.

Activation of the signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems no agent for activation is necessary such as those systems that involve a label that is a radioactive label, an enzyme, and so forth. For enzyme systems addition of a substrate and/or a cofactor may be necessary.

In certain embodiments first and second labels may be employed and comprise a label pair. These label pairs may be, for example, a singlet oxygen generator or sensitizer and chemiluminescent reactant pair, an enzyme pair wherein a product of the first enzyme serves as a substrate for the second enzyme and a luminescent energy donor and acceptor pair, e.g., an energy donor or acceptor and a fluorescent compound. The signal will usually be initiated by and/or detected as electromagnetic radiation and will preferably be luminescence such as chemiluminescence, fluorescence, electroluminescence or phosphorescence.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the entactogen analyte present in a sample above the predetermined cut-off level. Temperatures during measurements generally range from about 10° to about 70° C., more usually from about 20° to about 45° C., more usually about 20° to about 25° C. In one approach standard curves are formed using known concentrations of the analytes to be screened. Calibrators and other controls may also be used.

The description below of certain exemplary embodiments of methods uses the language "and/or," which means that the method may or may not involve each item mentioned. This language is used for the sake of brevity. In general, a method will involve at least one antibody for an analyte, e.g., methylenedioxyamphetamine, and at least one enzyme conjugate that corresponds to that analyte, e.g., an enzyme conjugate of a methylenedioxyamphetamine.

One embodiment is a method for determining a compound selected from the group consisting of 3,4-methylenedioxyamphetamine (MDA), 3,4-methylenedioxy-methamphetamine (MDMA), 3,4-methylenedioxyethyl-amphetamine (MDEA) and 4-hydroxy-3-methoxy-methamphetamine (HMMA), said method comprising:

(a) providing in combination in a medium:

(i) a sample suspected of containing said compound and (ii) an antibody raised against a compound of the formula:

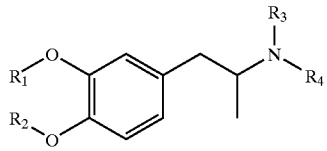

wherein: $R^1$ is H, lower alkyl, a protecting group, or is taken together with $R^2$ to form a ring, $R^2$ is H, lower alkyl, a protecting group, —(CH$^2$)$_n$SCH$_2$C(O)R$^6$ or —(CH$_2$)$_n$C(SO$_2$R$^6$)=CH$_2$, or is taken together with $R^1$ to form a ring, $R^3$ and $R^4$ are independently H or lower alkyl or a protecting group, or, when $R^1$ is taken together with $R^2$ to form a ring, at least one of $R^3$ or $R^4$ is —(CH$_2$)$_n$C(O)R$^5$, —C(O)(CH$_2$)$_n$R$^5$, —C(O)(CH$_2$)$_n$NHC(O)R$^5$, —C(O)(CH$_2$)$_n$NHC(O)(CH$_2$)$_n$SR$^5$, —(CH$_2$)$_n$C(SO$_2$R$^5$)=CH$_2$, —(CH$_2$)$_n$SCH$_2$C(O)R$^5$, —(CH$_2$)$_n$R$^5$, or —(CH$_2$)$_n$C(SO$_2$R$^5$)=CH$_2$, or when $R^1$ is not taken together with $R^2$ to form a ring, at least one of $R^1$ and $R^2$ is not H or lower alkyl, preferably, $R^3$ and $R^4$ are independently H or lower alkyl or a protecting group, or, when $R^1$ is taken together with $R^2$ to form a ring, at least one, preferably, one, of $R^3$ or $R^4$ is —C(O)(CH$_2$)$_n$R$^5$, —C(O)(CH$_2$)$_n$NHC(O)R$^5$, —C(O)(CH$_2$)$_n$NHC(O)(CH$_2$)$_n$SR$^5$, —(CH$_2$)$_n$C(SO$_2$R$^5$)=CH$_2$, —(CH$_2$)$_n$SCH$_2$C(O)R$^5$, or —(CH$_2$)$_n$C(SO$_2$R$^5$)=CH$_2$, or when $R^1$ is not taken together with $R^2$ to form a ring, $R^2$ is —(CH$^2$)$_n$SCH$_2$C(O)R$^6$ or —(CH$_2$)$_n$C(SO$_2$R$^6$)=CH$_2$, $R^5$ is —NH-protein or other immunogenic carrier such as, e.g., non-poly(amino acid) immunogenic carrier, $R^6$ is —NH-protein or other immunogenic carrier such as, e.g., non-poly(amino acid) immunogenic carrier, n is an integer from 1 to 5, and (b) examining said medium for the presence a complex comprising said compound and said antibody, the presence thereof indicating the presence of said compound in said sample.

One embodiment is a method for determining amphetamine and/or methamphetamine and/or methylenedioxyethamphetamine in a sample suspected of containing methylenedioxyamphetamine and/or methylenedioxymethamphetamine and/or methylenedioxyethamphetamine, said method comprising:

(a) providing in combination in a medium:

(i) said sample, (ii) an antibody for methylenedioxyamphetamine, and/or (iii) an antibody for methylenedioxymethamphetamine, and/or (iv) an antibody for methylenedioxyethamphetamine, and (v) a compound of the formula:

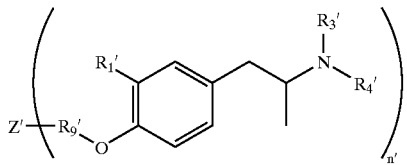

wherein:

$R^{1'}$ is H, or methyl or ethyl, preferably, H, $R^{3'}$ is H, $R^{4'}$ is H, or methyl or ethyl, $R^{9'}$ is —(CH$_2$)$_n$SCH$_2$C(O)R$^{6'}$, —(CH$_2$)$_n$R$^{6'}$, or —(CH$_2$)$_n$C(SO$_2$R$^{6'}$)=CH$_2$, preferably, $R^{9'}$ is —(CH$_2$)$_n$SCH$_2$C(O)R$^{6'}$ or —(CH$_2$)$_n$C(SO$_2$R$^{6'}$)=CH$_2$, $R^{6'}$ is Z', which is an enzyme, such as, e.g., G6PDH, n' is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

One embodiment is a method for determining methylenedioxyamphetamine and/or methylenedioxymethamphetamine and/or methylenedioxyethamphetamine in a sample suspected of containing methylenedioxyamphetamine and/or methylenedioxy-methamphetamine and/or methylenedioxyethamphetamine, said method comprising:

(a) providing in combination in a medium:

(i) said sample, (ii) an antibody for methylenedioxyamphetamine, and/or (iii) an antibody for methylenedioxymethamphetamine, and/or (iv) an antibody for methylenedioxyethamphetamine, and (v) a compound of the formula:

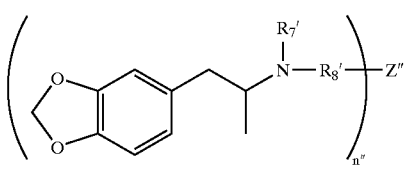

wherein:

$R^{7'}$ is H, or methyl, or ethyl, $R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})=CH_2$, —$(CH_2)_nSCH_2C(O)R^{5'}$, —$(CH_2)_nR^{5'}$, or —$(CH_2)_nC(SO_2R^{5'})=CH_2$, preferably, $R^{8'}$ is —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})=CH_2$, —$(CH_2)_nSCH_2C(O)R^{5'}$, or —$(CH_2)_nC(SO_2R^{5'})=CH_2$, $R^{5'}$ is Z", which is an enzyme, such as, e.g., G6PDH, n" is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxymethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

One embodiment is a method for determining methylenedioxyamphetamine and/or methylenedioxymethamphetamine and/or methylenedioxyethamphetamine in a sample suspected of containing methylenedioxyamphetamine and/or methylenedioxy-methamphetamine and/or methylenedioxyethamphetamine, said method comprising:

(a) providing in combination in a medium:
 (i) said sample,
 (ii) a conjugate of an enzyme and a methylenedioxyamphetamine analog and/or a conjugate of an enzyme and a methylenedioxymethamphetamine analog and/or a conjugate of an enzyme and a methylenedioxyethamphetamine analog,
 (iii) an antibody for methylenedioxyamphetamine, said antibody being raised against a compound of the formula:

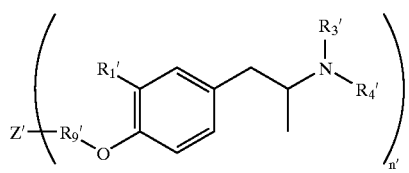

wherein:
$R^{1'}$ is H, or methyl or ethyl, preferably, H,
$R^{3'}$ is H,
$R^{4'}$ is H,
$R^{9'}$ is —$(CH_2)_nSCH_2C(O)R^{6'}$, —$(CH_2)_nR^{6'}$, or —$(CH_2)_nC(SO_2R^{6'})=CH_2$, preferably, $R^{9'}$ is —$(CH_2)_nSCH_2C(O)R^{6'}$ or —$(CH_2)_nC(SO_2R^{6'})=CH_2$, $R^{6'}$ is Z', which is an immunogenic protein or a non-poly (amino acid) immunogenic carrier, n' is an integer between 1 and the molecular weight of said immunogenic protein or said immunogenic carrier divided by about 500; and/or (iv) an antibody for methylenedioxymethamphetamine, said antibody being raised against a compound of the formula:

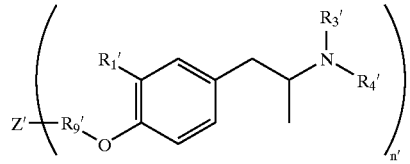

wherein:
$R^{1'}$ is H, or methyl or ethyl, preferably, H,
$R^{3'}$ is H,
$R^{4'}$ is methyl,
$R^{9'}$ is —$(CH_2)_nSCH_2C(O)R^{6'}$, —$(CH_2)_nR^{6'}$, or —$(CH_2)_nC(SO_2R^{6'})=CH_2$, preferably, $R^{9'}$ is —$(CH_2)_nSCH_2C(O)R^{6'}$ or —$(CH_2)_nC(SO_2R^{6'})=CH_2$, $R^{6'}$ is Z', which is an immunogenic protein or a non-poly (amino acid) immunogenic carrier, n' is an integer between 1 and the molecular weight of said immunogenic protein or said immunogenic carrier divided by about 500; and/or (v) an antibody for methylenedioxyethamphetamine, said antibody being raised against a compound of the formula:

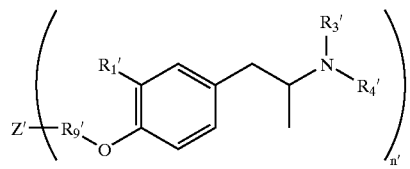

wherein:
$R^{1'}$ is H, or methyl or ethyl, preferably, H,
$R^{3'}$ is H,
$R^{4'}$ is ethyl,
$R^{9'}$ is —$(CH_2)_nSCH_2C(O)R^{6'}$, —$(CH_2)_nR^{6'}$, or —$(CH_2)_nC(SO_2R^{6'})=CH_2$, preferably, $R^{9'}$ is —$(CH_2)_nSCH_2C(O)R^{6'}$ or —$(CH_2)_nC(SO_2R^{6'})=CH_2$, $R^{6'}$ is Z', which is an immunogenic protein or a non-poly (amino acid) immunogenic carrier, n' is an integer between 1 and the molecular weight of said immunogenic protein or said immunogenic carrier divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

Another embodiment is a method for determining methylenedioxyamphetamine and/or methylenedioxymethamphetamine in a sample suspected of containing methylenedioxyamphetamine and/or methylenedioxymethamphetamine, said method comprising:

(a) providing in combination in a medium:
    (i) said sample,
    (ii) a conjugate of an enzyme and an methylenedioxyamphetamine analog and/or a conjugate of an enzyme and a methylenedioxymethamphetamine analog and/or a conjugate of an enzyme and a methylenedioxyethamphetamine analog,
    (iii) an antibody for methylenedioxyamphetamine, said antibody being raised against a compound of the formula:

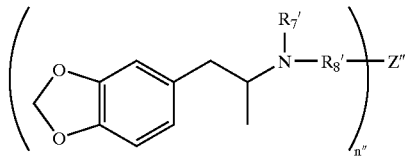

wherein:
$R^{7'}$ is H,
$R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(C_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$, $R^{5'}$ is Z″, which is an immunogenic protein or a non-poly (amino acid) immunogenic carrier, n″ is an integer between 1 and the molecular weight of said immunogenic protein or said immunogenic carrier divided by about 500; and/or (iv) an antibody for methylenedioxymethamphetamine, said antibody being raised against a compound of the formula:

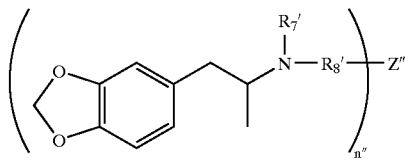

wherein:
$R^{7'}$ is methyl,
$R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$, $R^{5'}$ is Z″, which is an immunogenic protein or a non-poly (amino acid) immunogenic carrier, n″ is an integer between 1 and the molecular weight of said immunogenic protein or said immunogenic carrier divided by about 500; and/or (v) an antibody for methylenedioxyethamphetamine, said antibody being raised against a compound of the formula:

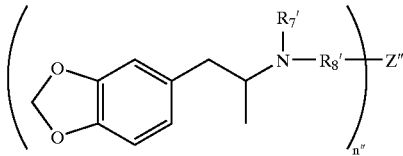

wherein:
$R^{7'}$ is ethyl,
$R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$, $R^{5'}$ is Z″, which is an immunogenic protein or a non-poly (amino acid) immunogenic carrier, n″ is an integer between 1 and the molecular weight of said immunogenic protein or said immunogenic carrier divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said amphetamine and/or methamphetamine and/or methylenedioxyethamphetamine in said sample.

The examining may comprise measuring signal from the enzyme, the amount thereof being related to the presence of the methylenedioxyamphetamine and/or methylenedioxymethamphetamine and/or methylenedioxyethamphetamine in the sample. The method may be a homogeneous method and the medium is examined for the amount of the signal. The method may be a heterogeneous method and the complex, if present, is separated from the medium and the medium or the complex is examined for the amount of the signal. The enzyme may be glucose-6-phosphate dehydrogenase.

Kits

Another aspect of the present invention relates to kits useful for conveniently performing an assay for the determination of an entactogen analyte such as, for example, 3,4-methylenedioxyamphetamine (MDA), 3,4-methylenedioxy-methamphetamine (MDMA), 3,4-methylenedioxyethyl-amphetamine (MDEA) and 4-hydroxy-3-methoxy-methamphetamine (HMMA). The kit comprises (a) an antibody raised against a conjugate of an immunogen such as, e.g., a protein, and a compound of Formula I, Formula II or Formula III and (b) ancillary reagents for determining the compound. The kit may further comprise a label conjugate of the compound of Formula I, Formula II or Formula III above.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

The description below of certain exemplary embodiments of kits uses the language "and/or," which means that the kit may or may not contain each item mentioned. This language is used for the sake of brevity. In general, a kit will include at least one antibody for an analyte, e.g., methylenedioxyamphetamine, and at least one enzyme conjugate that corresponds to that analyte, e.g., an enzyme conjugate of a methylenedioxyamphetamine.

A particular embodiment is a kit comprising in packaged combination:
(i) an antibody for methylenedioxyamphetamine, and/or
(ii) an antibody for methylenedioxymethamphetamine, and/or
(iii) an antibody for methylenedioxyethamphetamine, and
(iv) a compound of the formula:

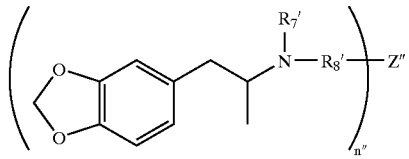

wherein:
$R^{7'}$ is H, or methyl, or ethyl,
$R^{8'}$ is $-(CH_2)_n C(O)R^{5'}$, $-C(O)(CH_2)_n R^{5'}$, $-C(O)(CH_2)_n NHC(O)R^{5'}$, $-C(O)(CH_2)_n NHC(O)(CH_2)_n SR^5$, $-(CH_2)_n C(SO_2 R^{5'})=CH_2$, $-(CH_2)_n SCH_2 C(O)R^{5'}$, $-(CH_2)_n R^{5'}$, or $-(CH_2)_n C(SO_2 R^{5'})=CH_2$, preferably, $R^{8'}$ is $-C(O)(CH_2)_n R^{5'}$, $-C(O)(CH_2)_n NHC(O)R^{5'}$, $-C(O)(CH_2)_n NHC(O)(CH_2)_n SR^5$, $-(CH_2)_n C(SO_2 R^{5'})=CH_2$, $-(CH_2)_n SCH_2 C(O)R^{5'}$, or $-(CH_2)_n C(SO_2 R^{5'})=CH_2$,
$R^{5'}$ is Z'', which is an enzyme, such as, e.g., G6PDH,
n'' is an integer between 1 and the molecular weight of said enzyme divided by about 500.

Another embodiment of a kit comprises in packaged combination:
(i) an antibody for methylenedioxyamphetamine,
(ii) an antibody for methylenedioxymethamphetamine, and/or
(iii) an antibody for methylenedioxyethamphetamine, and
(iv) a compound of the formula:

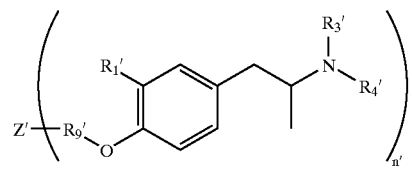

wherein:
$R^{1'}$ is H, or methyl or ethyl, preferably, H,
$R^{3'}$ is H,
$R^{4'}$ is H,
$R^{9'}$ is $-(CH_2)_n SCH_2 C(O)R^{6'}$, $-(CH_2)_n R^{6'}$, or $-(CH_2)_n C(SO_2 R^{6'})=CH_2$, preferably, $R^{9'}$ is $-(CH_2)_n SCH_2 C(O)R^{6'}$ or $-(CH_2)_n C(SO_2 R^{6'})=CH_2$,
$R^{6'}$ is Z', which is an immunogenic protein or a non-poly (amino acid) immunogenic carrier,
n' is an integer between 1 and the molecular weight of said immunogenic protein or said immunogenic carrier divided by about 500.

Another embodiment of a kit comprises in packaged combination:
(i) a conjugate of an enzyme and a methylenedioxyamphetamine analog and/or a conjugate of an enzyme and a methylenedioxymethamphetamine analog, and/or a conjugate of an enzyme and a methylenedioxyethamphetamine analog, and
(ii) an antibody for methylenedioxyamphetamine, said antibody being raised against a compound of the formula:

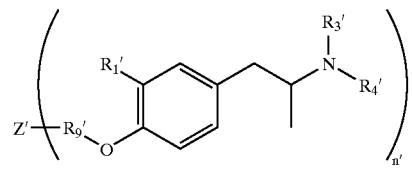

wherein:
$R^{1'}$ is H, or methyl or ethyl, preferably, H,
$R^{3'}$ is H,
$R^{4'}$ is H,
$R^{9'}$ is $-(CH_2)_n SCH_2 C(O)R^{6'}$, $-(CH_2)_n R^{6'}$, or $-(CH_2)_n C(SO_2 R^{6'})=CH_2$, preferably, $R^{9'}$ is $-(CH_2)_n SCH_2 C(O)R^{6'}$ or $-(CH_2)_n C(SO_2 R^{6'})=CH_2$,
$R^{6'}$ is Z', which is an immunogenic protein or a non-poly (amino acid) immunogenic carrier,
n' is an integer between 1 and the molecular weight of said immunogenic protein or said immunogenic carrier divided by about 500; and/or (iii) an antibody for methylenedioxymethamphetamine, said antibody being raised against a compound of the formula:

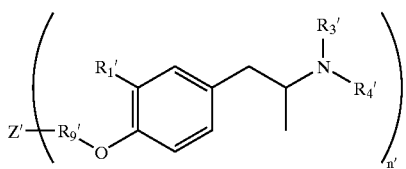

wherein:

$R^{1'}$ is H, or methyl or ethyl, preferably, H, $R^{3'}$ is H, $R^{4'}$ is methyl, $R^{9'}$ is —$(CH_2)_nSCH_2C(O)R^{6'}$, —$(CH_2)_nR^{6'}$, or —$(CH_2)_nC(SO_2R^{6'})$=$CH_2$, preferably, $R^{9'}$ is —$(CH_2)_nSCH_2C(O)R^{6'}$ or —$(CH_2)_nC(SO_2R^{6'})$=$CH_2$, $R^{6'}$ is Z', which is an immunogenic protein or a non-poly (amino acid) immunogenic carrier, n' is an integer between 1 and the molecular weight of said immunogenic protein or said immunogenic carrier divided by about 500, and/or (iv) an antibody for methylenedioxyethamphetamine, said antibody being raised against a compound of the formula:

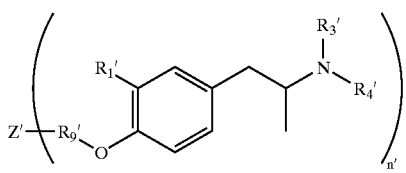

wherein:

$R^{1'}$ is H, or methyl or ethyl, preferably, H, $R^{3'}$ is H, $R^{4'}$ is ethyl, $R^{9'}$ is —$(CH_2)_nSCH_2C(O)R^{6'}$, —$(CH_2)_nR^{6'}$, or —$(CH_2)_nC(SO_2R^{6'})$=$CH_2$, preferably, $R^{9'}$ is —$(CH_2)_nSCH_2C(O)R^{6'}$ or —$(CH_2)_nC(SO_2R^{6'})$=$CH_2$, $R^{6'}$ is Z', which is an immunogenic protein or a non-poly (amino acid) immunogenic carrier, n' is an integer between 1 and the molecular weight of said immunogenic protein or said immunogenic carrier divided by about 500.

Another embodiment is a kit comprising in packaged combination:

(i) a conjugate of an enzyme and a methylenedioxyamphetamine analog and/or a conjugate of an enzyme and a methylenedioxymethamphetamine analog, and/or a conjugate of an enzyme and a methylenedioxyethamphetamine analog, and (ii) an antibody for methylenedioxyamphetamine, said antibody being raised against a compound of the formula:

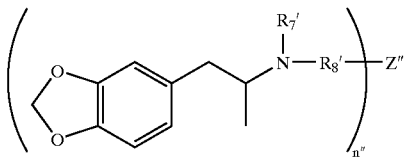

wherein:

$R^{7'}$ is H, $R^{8'}$ is —$(CH_2)_nC(O)R^{5'}$, —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$C(O)(CH_2)_nNHC(O)(CH_2)_nSR^5$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$, $R^{5'}$ is Z", which is an immunogenic protein or a non-poly (amino acid) immunogenic carrier, n" is an integer between 1 and the molecular weight of said immunogenic protein or said immunogenic carrier divided by about 500; and/or (iii) an antibody for methylenedioxymethamphetamine, said antibody being raised against a compound of the formula:

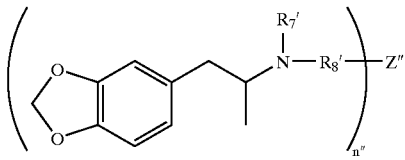

wherein:

$R^{7'}$ is methyl, $R^{8'}$ is —$(CH_2)_nC(O)R^{5'}$, —$C(O)(CH_2)_nR^{5'}$, —$C(O)(CH_2)_nNHC(O)R^{5'}$, —$(CH_2)_nC(SO_2R^{5'})$=$CH_2$, —$(CH_2)_nSCH_2C(O)R^{5'}$, —$(CH_2)_nR^{5'}$, or —$(CH_2)_nC(SO_2R^{5'})$=$CH_2$, preferably, $R^{8'}$ is —$C(O)(CH_2)_nR^{5'}$, —$C(O)(CH_2)_nNHC(O)R^{5'}$, —$(CH_2)_nC(SO_2R^{5'})$=$CH_2$, —$(CH_2)_nSCH_2C(O)R^{5'}$, or —$(CH_2)_nC(SO_2R^{5'})$=$CH_2$, $R^{5'}$ is Z", which is an immunogenic protein or a non-poly (amino acid) immunogenic carrier, n" is an integer between 1 and the molecular weight of said immunogenic protein or said immunogenic carrier divided by about 500, and/or (iv) an antibody for methylenedioxyethamphetamine, said antibody being raised against a compound of the formula:

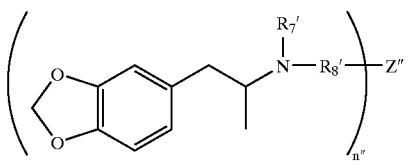

wherein:

$R^{7'}$ is ethyl, $R^{8'}$ is $-(CH_2)_nC(O)R^{5'}$, $-C(O)(CH_2)_nR^{5'}$, $-C(O)(CH_2)_nNHC(O)R^{5'}$, $-C(O)(CH_2)_nNHC(O)(CH_2)_nSR^5$, $-(CH_2)_nC(SO_2R^{5'})=CH_2$, $-(CH_2)_nSCH_2C(O)R^{5'}$, $-(CH_2)_nR^{5'}$, or $-(CH_2)_nC(SO_2R^{5'})=CH_2$, preferably, $R^{8'}$ is $-C(O)(CH_2)_nR^{5'}$, $-C(O)(CH_2)_nNHC(O)R^{5'}$, $-C(O)(CH_2)_nNHC(O)(CH_2)_nSR^5$, $-(CH_2)_nC(SO_2R^{5'})=CH_2$, $-(CH_2)_nSCH_2C(O)R^{5'}$, or $-(CH_2)_nC(SO_2R^{5'})=CH_2$, $R^{5'}$ is Z", which is an immunogenic protein or a non-poly(amino acid) immunogenic carrier, n" is an integer between 1 and the molecular weight of said immunogenic protein or said immunogenic carrier divided by about 500.

EXAMPLES

The invention is demonstrated further by the following illustrative examples. Parts and percentages recited herein are by weight unless otherwise specified. Temperatures are in degrees centigrade (° C.).

Analytical thin layer chromatography (TLC) was the usual analysis method and performed on Analtech Uniplate Silica Gel GF (0.25 mm) glass-backed plates using the specified solvent. The spots on TLC were visualized by ultraviolet light (short and/or long wave) and/or iodine vapors. Flash chromatography was carried out on Whatman silica gel 60 Å (230–400 mesh). All chemicals were obtained from Sigma Chemical Company (St. Louis, Mo.), Aldrich Chemical Company (St. Louis, Mo.), Fluka (Milwaukee, Wis.) and used as received. $^1$H-NMR and $^{13}$C-NMR spectra routinely recorded on a Bruker Ultrashiel™-400 (400 MHz) spectrometer (Bruker, Billerica Mass.). Chemical shift were reported in parts per million (ppm, δ) and related to tetramethylsilane or with deuterated solvent as internal reference. NMR abbreviations used are s (singlet), d (doublet), and m (multiplet). Mass spectra were obtained at the Mass Spectrometry Laboratory, University of California at Berkeley, Berkeley, Calif.

Melting points were determined on a Hoover capillary apparatus and are uncorrected. Infrared spectra were recorded on a Perkin-Elmer 297IR spectrometer. UV-visible absorption spectra were done on a HP 8452A diode array spectrophotometer. Fluorescence measurements were done on a Spex fluorolog spectrophotometer or a Perkin Elmer 650-40 spectrophotometer.

The following abbreviations have the meanings set forth below:

g—grams
mg—milligrams
mL—milliliters
μL—microliters
mmol—millimoles
DMF—dimethyl formamide
THF—tetrahydrofuran
NMR—nuclear magnetic resonance spectroscopy
MHz—megahertz
EDAC—1-ethyl-3-(3-dimethylaminopropyl)carbodiimide hydrochloride (Sigma Chemical Company)
MeOH—methanol
FAB-MS—fast atom bombardment—mass spectrometry
DI water—deionized water
BCA Protein Concentration Assay—Pierce Chemical Company
TNBS—2,4,6-trinitrobenzene sulfonic acid
KLH—keyhole limpet hemocyanin
NHS—N-hydroxysuccinimic ester
THF—tetrahydrofuran
tBoc$_2$O—di-tert-butyldicarbonate
TFA—trifluoroacetic acid Preparation of Antibodies The following method may be employed to prepare polyclonal antibodies: Antiserum containing antibodies is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

The following procedure may be employed to prepare monoclonal antibodies: Monoclonal antibodies were produced according to the standard techniques of Köhler and Milstein, Nature 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained. Alternatively, the spleen cells of an non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In general, antibodies can be purified by known techniques such as chromatography, e.g., DEAE chromatography, ABx chromatography, and the like, filtration, and so forth.

Preparation of Compound (7)

To a solution of MDMA (1) (45 mg) in DMF (10 mL) was added NaH (27 mg). The reaction mixture was stirred at room temperature for 20 minutes. Methyl bromoacetate (50 mg) was added to the mixture. The mixture was stirred at room temperature for 4 hours. DMF was removed by rotary evaporation and water (10 mL) was added. The aqueous phase was extracted with ethyl acetate (4×25 mL). The combined organic phases were dried over MgSO$_4$, filtered and concentrated. The residue was purified by flash column chromatography using ethyl acetate/hexane (2/3) as an eluent to give the desired product (7) (48 mg, 92% yield); FAB-MS: MH⁺ (266); $^1$H-NMR (CDCl$_3$, 400 MHz) δ: 6.64 (m, 3H), 5.88 (s, 2H), 3.70 (s, 3H), 3.28 (s, 2H), 2.92 (m, 2H), 2.38 (s, 3H), 2.25 (m, 1H), 0.91 (d, J=6.3 Hz, 3H); $^{13}$C-NMR (CDCl$_3$, 100 MHz) δ: 1.72.5, 149.9, 146.1, 134.2, 122.4, 109.9, 108.5, 101.2, 61.0, 55.3, 52.2, 39.8, 38.9, 14.7.

Preparation of Compound (8)

To a solution of 7 (20 mg, 0.0754 mmol) in MeOH (5 mL) and H$_2$O (0.5 mL) was added K$_2$CO$_3$ (104 mg). The reaction mixture was stirred at room temperature for 4 hours. HCl (6N) was added to maintain the pH value to 3–4. Most of MeOH and H$_2$O were removed by rotary evaporation. The residue was purified by flash column chromatography using CH$_2$Cl$_2$/MeOH (17/3) as an eluent to give the desired product (8) (20 mg); FAB-MS: MH⁺ (252); $^1$H-NMR (CD$_3$OD, 400 MHz) δ: 6.76 (m, 3H), 5.92 (s,2H), 4.00 (m, 2H), 3.66 (m, 1H), 3.23 (m, 1H), 2.94 (s, 3H), 2.82 (m, 1H), 1.22 (d, J=6.6 Hz, 3H).

Preparation of MDMA-KLH Immunogen (10)

To a solution of 8 (8 mg, 0.0278 mmol) in DMF (0.5 mL) was added EDAC (18 mg, 0.0938 mmol) and NHS (14 mg, 0.121 mmol). The reaction was stirred at room temperature under argon for 2.5 hours. The progress of the reaction was monitored by TLC (silica gel, MeOH/CH$_2$Cl$_2$=1/9). The activated hapten (9) was added drop wise under argon to 6 mL of sodium phosphate solution (0.1M, pH=8.0) of KLH (20 mg) at 0° C. under argon. The pH value changed during the addition and 0.1 N of NaOH aqueous solution was used to maintain the pH at 8.0. After completed the addition, the solution was allowed to stir at room temperature for 1.5 hours. The conjugate (10) was dialyzed against Dulbecco's phosphate buffered saline (pH=7.0, 3 Liters) prepared from Dulbecco's phosphate buffered saline (Sigma buffer, 400 mL) diluting with DI water (2600 mL) at 4° C. for 4 hours. The dialyzing procedure was repeated three times with fresh buffer solution for 16, 24 and 40 hours each. Finally, the conjugate was dialyzed with sodium phosphate buffer solution (10 mM, pH=7.0) two times (3 hours and 4 hours). The concentration of protein was measured by using BCA Protein Concentration Assay and the TNBS method was used for hapten number determination. The immunogen (10) has a concentration of 2.32 mg/mL with the hapten number of 1087, and used for the immunization of mice for antibody production.

Preparation of Compound (11)

To a solution of MDA (4) (30 mg, 0.139 mmol) in DMF (18 mL) was added NaH (18 mg, 0.713 mmol). The reaction mixture was stirred at room temperature for 20 minutes. Methyl bromoacetate (32 mg, 0.209 mmol) was added to the mixture. The mixture was stirred at room temperature for 4 hours. DMF was removed by rotary evaporation and water (10 mL) was added. The aqueous phase was extracted with ethyl acetate (4×20 mL). The combined organic phase was dried over MgSO$_4$, filtered and concentrated. The residue was purified by flash column chromatography using ethyl acetate/hexane (2/3) as an eluent to give the desired product (11) (23 mg, 66% yield); FAB-MS: MH⁺ (252); $^1$H-NMR (CDCl$_3$, 400 MHz) δ: 6.66 (m, 3H), 5.90 (s, 2H), 3.76 (m, 1H), 3.68 (s, 3H), 3.41 (m, 2H), 2.84 (m, 1H), 2.63 (m, 1H), 2.52 (m, 1H), 1.01 (d, J=6.2 Hz, 3H); $^{13}$C-NMR (CDCl$_3$, 100 MHz) δ: 173.3, 148.0, 146.4, 133.1, 122.6, 109.9, 108.6, 101.2, 54.6, 52.8, 52.2, 48.9, 43.8, 20.23.

Preparation of Compound (12)

To a solution of 11 (23 mg, 0.0951 mmol) in MeOH (12 mL) was added NH$_4$OH (1 mL). The reaction mixture was stirred at room temperature for 16 hours. Most of MeOH and NH$_4$OH were removed by rotary evaporation. The residue was further dried under high vacuum for removing trace amount of MeOH and NH$_4$OH. The residue was dissolved in CH$_2$Cl$_2$/MeOH (9/1) and purified by flash column chromatography using CH$_2$Cl$_2$/MeOH (3/1) as an eluent to give the desired product (12) (20.8 mg, 96% yield); FAB-MS: MH⁺ (237); $^1H$-NMR (CDCl$_3$, 400 MHz) δ: 7.03 (m, 1H), 6.68 (m, 3H), 5.92 (s, 2H), 5.70 (m, 1H), 3.11 (m, 2H), 2.81 (m, 1H), 2.55 (m, 1H), 1.05 (d, J=6.3 Hz, 3H).

Preparation of MDA-KLH Immunogen (14)

To a solution of 12 (8 mg, 0.0337 mmol) in DMF (0.5 mL) was added EDAC (19 mg, 0.0991 mmol) and NHS (19 mg, 0.165 mmol). The reaction was stirred at room temperature under argon for 16 hours. The progress of the reaction was monitored by TLC (silica gel, MeOH/CH$_2$Cl$_2$=1/9). The activated hapten (13) was added drop wise under argon to 5 mL of sodium phosphate solution (0.1M, pH=8.0) of KLH (20 mg) at 0° C. under argon. The pH value changed during the addition and 0.1 N of NaOH aqueous solution was used to maintain the pH=8.0. After completed the addition, the conjugate was allowed to stir at room temperature for 4 hours. The conjugate (14) was dialyzed against Dulbecco's phosphate buffered saline (pH=7.0, 3 Liters) prepared from Dulbecco's phosphate buffered saline (Sigma buffer, 400 mL) diluting with DI water (2600 mL) at 4° C. for 4 hours. The dialyzing procedure was repeated with fresh buffer solution for 16, 24 and 40 hours. Finally, the conjugate was dialyzed with sodium phosphate buffer solution (10 mM, pH=7.0) two times (3 hours and 4 hours). The concentration of protein was measured by using BCA Protein Concentration Assay and the TNBS method was used for hapten number determination. The immunogen (14) has a concentration of 2.63 mg/mL with the hapten number of 1490, and used for the immunization of mice for antibody production.

Preparation of Compound (15)

To a stirred solution of MDMA (1) (15.7 mg, 0.0684 mmol) in THF (8 mL) was added diisopropylethylamine (100 μL, 0.574 mmol). The reaction was stirred at room temperature for 60 minutes. Bromoacetic acid N-hydroxy succinimide (48 mg, 0.202 mmol) was added to the reaction mixture under argon. The reaction mixture was stirred at room temperature for 1 hour. Water (10 mL) was added and most of the THF was removed by rotary evaporation. The aqueous phase was extracted with CH$_2$Cl$_2$ (3×25 mL). The combined organic phases were washed with water (10 mL) and dried over MgSO$_4$. The organic phase was filtered and evaporated to dryness by rotary evaporation. The residue was purified by flash column chromatography (silica gel) using ethyl acetate/hexane (3/7) as an eluent to give the desired product (15) (16 mg, 75% yield); FAB-MS: MH⁺ (314); $^1$H-NMR (CDCl$_3$, 400 MHz) δ: 6.62 (m, 3H), 5.93–5.89 (m, 2H), 4.86, 3.45 (m, 1H), 3.98 (m, 1H), 3.71 (m, 1H), 3.49 (m, 1H), 2.86 (s, 3H), 2.68 (m, 2H), 1.28, 1.11 (m, 3H).

Preparation of Compound (16)

To a stirred solution of MDMA (1) (16 mg, 0.0697 mmol) in THF (10 mL) was added diisopropylethylamine (100 μL, 0.574 mmol). The reaction was stirred at room temperature for 60 minutes. Bromoacetylglycine N-hydroxy succinic ester (61 mg, 0.208 mmol) was added to the reaction mixture under argon. The reaction mixture was stirred at room temperature for 1 hour. Water (10 mL) was added and most of the THF was removed by rotary evaporation. The aqueous phase was extracted with $CH_2Cl_2$ (3×25 mL). The combined organic phase were washed with water (10 mL) and dried over $MgSO_4$. The organic phase was filtered and evaporated to dryness by rotary evaporation. The residue was purified by flash column chromatography (silica gel) using ethyl acetate/hexane (3/7) as an eluent to give the desired product (16) (15 mg, 58% yield); FAB-MS: $MH^+$ (371); $^1$H-NMR ($CDCl_3$, 400 MHz) δ: 7.60 (m, NH), 6.69 (m, 3H), 5.91 (s, 2H), 4.86 (m, 1H, NH), 4.05–3.82 (m, 4H), 3.50 (m, 1H), 2.88, 2.76 (s, 3H), 2.69 (m, 2H), 1.24–1.12 (d, 3H).

Preparation of Compound (17)

To a stirred solution of MDMA (1) (20.9 mg, 0.091 mmol) in THF (5 mL) was added NaH (12 mg, 0.475 mmol). The reaction was stirred at room temperature for 15 minutes. 1,3-Dibromo-2-(methylsulfonyl)propane (31 mg, 0.11 mmol) was added to the reaction mixture. The reaction mixture was stirred at 0° C. for 40 minutes. TLC analysis of the mixture showed that starting material MDMA disappeared, and a new and less polar spot displayed. Water (0.1 mL) was added and most of the THF was removed by rotary evaporation under reduced pressure. The residue was purified by flash column chromatography (silica gel) using ethyl acetate/hexane (1/1) as an eluent to give the desired product (17) (26 mg, 92% yield); FAB-MS: $MH^+$ (312); $^1$H-NMR ($CDCl_3$, 400 MHz) δ: 6.64 (m, 3H), 6.27 (s, 1H), 5.90 (s, 2H), 5.82 (s, 1H), 3.42 (m, 2H), 3.01 (m, 1H), 2.80 (s, 3H), 2.74 (m, 1H), 2.45 (m, 1H), 2.17 (s, 3H), 0.96 (d, J=6.6 Hz, 3H); $^{13}$C-NMR ($CDCl_3$, 100 MHz) δ: 148.3, 148.0, 146.2, 134.2, 127.6, 122.3, 109.8, 108.5, 101.2, 61.1, 55.3, 43.5, 39.7, 35.1, 14.00.

Preparation of Compound (18)

To a stirred solution of MDA (4) (19 mg, 0.0881 mmol) in THF (10 mL) was added diisopropylethylamine (120 μL, 0.689 mmol). The reaction was stirred at room temperature for 60 minutes. Bromoacetic acid N-hydroxy succinimide (62.5 mg, 0.2637 mmol) was added to the reaction mixture under argon. The reaction mixture was stirred at room temperature for 1 hour. Water (10 mL) was added and most of the THF was removed by rotary evaporation. The aqueous phase was extracted with $CH_2Cl_2$ (3×30 ml). The combined organic phases were washed with water (10 mL) and dried over $MgSO_4$. The organic phase was filtered and evaporated to dryness by rotary evaporation. The residue was purified by flash column chromatography (silica gel) using ethyl acetate/hexane (2/3) as an eluent to give the desired product (18) (25 mg, 95% yield); FAB-MS: $MH^+$ (300); $^1$H-NMR ($CDCl_3$, 400 MHz) δ: 6.67 (m, 3H), 6.30 (m, 1H), 5.92 (s, 2H), 4.15 (m, 1H), 3.81 (s, 2H), 2.73(m, 1H), 2.66 (m, 1H), 1.13 (d, J=6.6 Hz, 3H).

Preparation of Compound (19)

To a stirred solution of MDA (4) (10 mg, 0.04636 mmol) in THF (5 mL) was added diisopropylethylamine (41 μL, 0.235 mmol). The reaction was stirred at room temperature for 30 minutes. Bromoacetylglycine N-hydroxy succinic ester (40.7 mg, 0.138 mmol) was added to the reaction mixture under argon. The reaction mixture was stirred at room temperature for 1 hour. Water (5 mL) was added and most of the THF was removed by rotary evaporation. The aqueous phase was extracted with $CH_2Cl_2$ (3×20 mL). The combined organic phases were washed with water (10 mL) and dried over $MgSO_4$. The organic phase was filtered and evaporated to dryness by rotary evaporation. The residue was purified by flash column chromatography (silica gel) using ethyl acetate/hexane (1/1) as an eluent to give the desired product (19) (8 mg, 48.3% yield); FAB-MS: $MH^+$ (357, 359); $^1$H-NMR ($CDCl_3$, 400 MHz) δ: 7.60 (m, NH), 6.64 (m, 3H), 6.00 (m, NH), 5.92 (s, 2H), 4.15 (m, 1H), 4.05 (m, 1H), 3.88 (b s, 3H), 2.69 (m, 2H), 1.12 (d, J=6.6 Hz, 3H);

Preparation of Compound (20)

To a stirred solution of MDA (4) (10 mg, 0.04636 mmol) in THF (5 mL) was added NaH (5 mg, 0.198 mmol). The reaction was stirred at room temperature for 15 minutes. 1,3-Dibromo-2-(methylsulfonyl)propane (14 mg, 0.05 mmol) was added to the reaction mixture at −20° C. The reaction mixture was stirred at −20° C. for 120 minutes. Water (0.1 mL) was added and most of the THF was removed by rotary evaporation under reduced pressure. The residue was purified by flash column chromatography (silica gel) using ethyl acetate/hexane (7/3) as an eluent to give the desired product (20) (11 mg, 80% yield); FAB-MS: $MH^+$ (298); $^1$H-NMR ($CDCl_3$, 400 MHz) δ: 6.72 (d, J=7.8 Hz, 1H), 6.64 (s, 1H), 6.60 (m 1H), 6.25 (s, 1H), 5.90 (s, 2H), 5.84 (s, 1H), 3.62 (dd, J=21.3, 15.0 Hz, 2H), 2.94 (s, 3H), 2.86 (m, 1H), 2.58 (m, 2H), 1.06 (d, J=6.3 Hz, 3H); $^{13}$C-NMR ($CDCl_3$, 100 MHz) δ: 149.4, 148.1, 146.5, 133.1, 126.1, 122.6, 109.9, 108.6, 101.3, 54.4, 46.9, 43.7, 43.3, 20.5.

Preparation of Compound (24)

To a solution of methylamine, hydrochloride (4.1 g, 60.72 mmol) in MeOH (50 mL) was added $NA_ACO$ (6.2 g, 58.5 mmol). The reaction was stirred at room temperature for 30 minutes. The reaction mixture was filtered through into a 100 mL of round-bottom flask containing 4-hydroxy-3-methyl phenyl acetone (22) (1.8 g, 10 mmol). The reaction mixture was refluxed for 2 hours and allowed to cool to room temperature. Sodium cyanoborohydride (628 mg, 10 mmol) was added to the mixture. The reaction mixture was refluxed for 5 hours and during this time the pH of the solution was maintained at neutrality by addition of 4M HCl in dioxane. The organic solvent was evaporated to dryness by rotary evaporation and the residue was dissolved in 20 mL of water. The solution was acidified with 6 N HCl to pH=2–3, extracted with ethyl acetate, then basified to pH=9–10 with 6 N NaOH, saturated with NaCl. The mixture was extracted with ethyl acetate, the combined organic extracts were dried over anhydrous $MgSO_4$ and filtered. The ethyl acetate was removed by evaporation to give an oil. The oily residue was purified by flash column chromatography (silica gel) using $MeOH/CH_2Cl_2$ (1/4) as an eluent to give the desired product (24) (532 mg, 27% yield); $^1$H-NMR ($CDCl_3$, 400 MHz) δ: 6.82 (d, J=7.9 Hz, 1H), 6.67 (s, 1H), 6.65 (d, J=7.4 Hz, 1H), 4.82 (s, OH), 3.85 (s, 3H), 3.46 (s, 3H), 2.75 (m, 1H), 2.587(m, 2H), 1.06 (d, J=6.2 Hz, 3H);

Preparation of Compound (25)

To a solution of 24 (513 mg, 2.627 mmol) in THF (30 mL) and $H_2O$ (20 mL) was added $tBoc_2O$ (1.21 g, 5.25 mmol) and $K_2CO_3$ (1.09 g, 7.89 mmol). The reaction was stirred at room temperature for 4 hours. Water (20 mL) was added and most of THF was removed by rotary evaporation. The aqueous phase was extracted with ethyl acetate (3×40 mL). The combined organic solvent was washed with water (30 mL) and dried over $MgSO_4$. The solvent was filtered and concentrated to dryness. The residue was purified by flash column chromatography using ethyl acetate/hexane (1/4) as an eluent to give the desired product (25) (632 mg, 82%); FAB-MS: $MH^+$ (296); $^1$H-NMR ($CDCl_3$, 400 MHz) δ: 6.80–6.52 (m, 3H), 5.96 (m, 1H, OH), 4.48, 4.19 (s, 1H), 3.78 (s, 3H), 2.68–2.50 (m, 5H), 1.48–1.46(m, 9H), 1.07–1.04 (m, 3H).

Preparation of Compound (26)

To a solution of 25 (100 mg, 0.3385 mmol) in DMF (10 mL) was added NaH (77 mg, 3.05 mmol). The reaction mixture was stirred at room temperature for 30 minutes. Methyl bromoacetate (73 mg, 0.474 mmol) was added to the mixture. The mixture was stirred at room temperature for 65 hours. DMF was removed by rotary evaporation and water (10 mL) was added. The aqueous phase was extracted with ethyl acetate (3×30 mL). The combined organic phases were washed with water (15 mL) and dried over $MgSO_4$. The organic phase were filtered and concentrated to dryness. The residue was purified by flash column chromatography using ethyl acetate/hexane (3/7) as an eluent to give the desired product (26) (38 mg, 31% yield); $^1$H-NMR ($CDCl_3$, 400 MHz) δ: 6.73 (m, 3H), 4.65 (s, 2H), 4.51, 4.24 (s, 1H), 3.86 (s, 3H), 3.77 (s, 3H), 2.79–2.55 (m, 5H), 1.38–1.32(m, 9H), 1.13 (bs, 3H).

Preparation of Compound (27)

To a solution of 26 (19 mg, 0.0517 mmol) in $CH_2Cl_2$ (2 mL) was added TFA (0.3 mL). The reaction mixture was stirred at room temperature for 120 minutes. TLC analysis of the reaction showed that starting material (26) disappeared and a new, polar spot displayed (silica gel, ethyl acetate/hexane=2/3). Most of $CH_2Cl_2$ and TFA were removed by rotary evaporation under reduced pressure. The residue was put in high vacuum to remove trace amount of TFA. This gave the desired product (27) (19 mg, 96% yield); $^1$H-NMR ($CDCl_3$, 400 MHz) δ: 7.54 (bs, NH), 6.72 (m, 3H), 4.66 (s, 2H), 3.83 (s, 3H), 3.79 (s, 3H), 3.40 (m, 1H), 3.03 (1H), 2.79 (m, 1H), 2.72 (bs, 3H), 1.32 (d, J=6.4 Hz, 3H).

Preparation of Compound (28)

To a solution of 27 (18 mg, 0.0472 mmol) in MeOH (5 mL) and water (1 mL) was added $K_2CO_3$ (33 mg, 0.239 mmol). The reaction mixture was stirred at room temperature for 180 minutes. 1 N HCl was added to adjust the pH values to 2–3. Most of MeOH, HCl and water were removed by rotary evaporation under vacuum. The residue was purified by flash column chromatography (silica gel) using $MeOH/CH_2Cl_2/AcOH$ (2/8/0.1) to give the desired product (28) (12 mg, 88% yield); $^1$H-NMR ($D_2O$, 400 MHz) δ: 6.77 (m, 3H), 4.58 (s, 2H), 3.72 (s, 3H), 3.38 (m, 1H), 2.87 (m, 1H), 2.71 (m, 1H), 2.57 (s, 3H), 1.13 (d, J=6.5 Hz, 3H).

Preparation of HMMA Immunogen (30)

To a solution of 28 (10 mg, 0.0345 mmol) in DMF (0.6 mL) was added EDAC (20 mg, 0.1043 mmol) and N-HS (19 mg, 0.165 mmol). The reaction was stirred at room temperature under argon for 2.5 hours. The activated hapten (29) was added drop wise under argon to 6 mL of sodium phosphate solution (0.1 M, pH=8.0) of KLH (20 mg) at 0° C. under argon. The pH value changed during the addition and 0.1 N of NaOH aqueous solution was used to maintain the pH to 8.0. After completed the addition, the conjugate was allowed to stir at 4° C. for 16 hours. The conjugate was dialyzed against Dulbecco's phosphate buffered saline (pH=7.0, 3 Liters) prepared from Dulbecco's phosphate buffered saline (Sigma buffer, 400 mL) diluting with DE water (2600 mL) at 4° C. for 4 hours. The dialyzing procedure was repeated with fresh buffer solution for 16, 24 and 40 hours. Finally, the conjugate was dialyzed with sodium phosphate buffer solution (10 mM, pH=7.0) two times (3 hours and 4 hours). The concentration of protein was measured by using BCA Protein Concentration Assay and the TNBS method was used for hapten number determination. The immunogen (30) has a concentration of 2.12 mg/mL with the hapten number of 1436, and used for the immunization of rats for antibody production.

Preparation of Compound (31)

To a solution of 25 (86 mg, 0.291 mmol) in toluene (15 mL) was added $K_2CO_3$ (200 mg) and dibromoethane (2 mL). The reaction was refluxed for 48 hours and stirred at room temperature for 66 hours. Water (10 mL) was added and toluene was separated. The aqueous phase was extracted with ethyl acetate (3×30 mL). The combined organic solvent was washed with water (20 mL) and dried over $MgSO_4$. The solvent was filtered and concentrated to dryness. The residue was purified by flash column chromatography using ethyl acetate/hexane (1/4) as an eluent to give the desired product (31) (62 mg, 53%); $^1$H-NMR ($CDCl_3$, 400 MHz) δ: 6.78 (m, 3H), 4.26 (t, J=6.6 Hz, 2H), 3.82 (s, 3H), 3.60 (t, J=6.7 Hz, 2H), 2.67 (m, 5H), 1.36 (m, 9H), 1.11 (bs, 3H).

Preparation of Compound (32)

To a solution of 31 (61 mg, 0.1516 mmol) in 95% ethanol (10 mL) was added potassium thioacetate (100 mg, 0.8756 mmol). The reaction was stirred at 55° C. under argon for 3 hours. Most of ethanol was removed by rotary evaporation. The residue was re-dissolved in 5 mL of $CH_2Cl_2$ and the precipitate was filtered off and washed with $CH_2Cl_2$ (2×10 mL). The combined organic solvent was concentrated to dryness. The residue was purified by flash column chromatography using ethyl acetate/hexane (3/7) as an eluent to give the desired product (32) (50 mg, 83%); $^1$H-NMR ($CDCl_3$, 400 MHz) δ: 6.82 (m, 1H), 6.64 (m, 2H), 4.08 (t, J=6.7 Hz, 2H), 3.82 (s, 3H), 3.25 (t, J=6.7 Hz, 2H), 2.65 (m, 5H), 2.33 (s, 3H), 1.33 (m, 9H), 1.10 (bs, 3H).

Preparation of Compound (33)

To a solution of 32 (48 mg, 0.1207 mmol) in $CH_2Cl_2$ (3 mL) was added TFA (0.4 mL). The reaction mixture was stirred at room temperature for 1.5 hours. TLC analysis of the mixture showed that starting material, 22 disappeared and a new spot displayed at baseline (silica gel, ethyl acetate/hexane=1/1). Most of $CH_2Cl_2$ and TFA were removed by rotary evaporation. The residue was put in high vacuum to remove traces of TFA. This gave the desired product, (33) (49 mg, 98%); $^1$H-NMR ($CDCl_3$, 400 MHz) δ: 6.86 (m, 1H), 6.68 (m, 2H), 4.09 (t, J=6.7 Hz, 2H), 3.82 (s, 3H), 3.37 (m, 1H), 3.26 (t, J=6.7 Hz, 2H), 3.07 (m, 1H), 2.70 (m, 4H), 2.34 (s, 3H), 1.28 (d, J=6.4 Hz, 3H); $^{13}$C-NMR ($CDCl_3$, 100 MHz) δ: 196.3, 150.3, 147.6, 128.8, 121.8, 117.5, 114.5, 113.3, 68.0, 57.7, 56.4, 39.6, 30.9, 28.6, 15.8.

Preparation of Bromoacetyl-KLH (35)

To a solution of bromoacetic acid NHS ester (8.6 mg, 0.0364 mmol) in DMF (0.3 mL) was added to a solution of KLH (40 mg) in $NaH_2PO_4$—$Na_2HPO_4$ buffer (pH=8.00, 0.1M, 4 mL) at 4° C. The reaction mixture was stirred in the cold-room (4° C.) for 16 hours. The mixture was chromatographed on a packed Sephadex G-50, eluting with $NaH_2PO_4$—$Na_2HPO_4$ buffer (pH=8.00, 0.1M) with a flow rate of 20 mL/hour. The eluted fractions (4 mL in volume for each fraction) from the column were monitored by UV at 280 nm. Fractions #10–13 were pooled to give 12 mL of bromoacetyl-KLH (35). The concentration of protein was measured by UV method and the TNBS method was used for hapten number determination. The conjugate has a concentration of 3.28 mg/mL with the hapten number of 925.

Preparation of HMMA Immunogen (36)

To a solution of 33 (25 mg, 0.06 mmol) in MeOH (0.5 mL) and water (0.1 mL) was added $K_2CO_3$ (20 mg). The reaction mixture was stirred at room temperature under argon for 1.5 hours. TLC analysis of the mixture showed that a new spot displayed to be product (34). $^1$H-NMR ($CDCl_3$, 400 MHz) δ: 6.84 (m, 1H), 6.68 (m, 2H), 4.26 (m, 2H), 3.84 (s, 3H), 3.11 (m, 2H), 3.07 (m, 1H), 2.73 (m, 1H), 2.58 (m, 2H), 2.38 (s, 3H), 1.05 (d, J=6.2 Hz, 3H).

To a solution of well-prepared bromoacetyl-KLH (35) (8 mL, 3.28 mg/mL, pH=8.00) was added the above reaction mixture slowly at 4° C. under argon. The reaction was stirred at 4° C. for 16 hours. The reaction mixture was chromatographed oil a Sephadex G-50 column, which was equilibrated with $NaH_2PO_4$—$Na_2HPO_4$ buffer (pH=7.20, 0.1 M, 200 mL). The column was eluted with $NaH_2PO_4$—$Na_2HPO_4$ buffer (pH=7.20, 0.1 M) with a flow rate of 20 mL/hour. The eluted fractions (4 mL in volume for each fraction) from the column were monitored by UV at 280 nm. Fractions #10–14 were collected to have 20 mL of immunogen (36). The concentration of immunogen was measured by using BCA Protein Concentration Assay. The Immunogen (36) has a concentration of 2.41 mg/mL with the hapten number of 925, and was used for the immunization of mice for antibody production.

Preparation of Compound (37)

To a solution of 25 (32 mg, 0.108 mmol) in THF (12 mL) was added NaH (19 mg, 0.752 mmol). The reaction mixture was stirred at room temperature for 10 minutes. 1,3-Dibromo-2-(methylsulfonyl)propane (43.8 mg, 0.156 mmol) was added to the reaction mixture, which was stirred at room temperature for 2 hours. Water (0.1 mL) was added and most of the THF was removed by rotary evaporation under reduced pressure. The residue was purified by flash column chromatography (silica gel) using ethyl acetate/hexane (1/2) as an eluent to give the desired product (37) (38 mg, 85.2% yield); FAB-MS: $MLi^+$ (420); $^1$H-NMR ($CDCl_3$, 400 MHz) δ: 6.82 (m, 1H), 6.70 (m, 2H), 6.45, 6.36 (s, 1H), 6.16, 6.03 (s, 1H), 4.85 (s, 2H), 3.90 (m, 1H), 3.82 (s, 3H), 3.14 (s, 3H), 2.70 (m, 5H), 1.32 (m, 9H), 1.11 (bs, 3H).

Preparation of Compound (38)

To a solution of 37 (19 mg, 0.046 mmol) in $CH_2Cl_2$ (2 mL) was added TFA (0.3 mL). The reaction mixture was stirred at room temperature for 120 minutes. TLC analysis of the reaction showed that starting material (26) disappeared and a new, polar spot displayed (silica gel, ethyl acetate/hexane=1/2). Most of $CH_2Cl_2$ and TFA were removed by rotary evaporation under reduced pressure. The residue was further dried under high vacuum to remove trace of TFA. This gave the desired product (38) (19 mg, 96% yield); $^1$H-NMR ($CDCl_3$, 400 MHz) δ: 6.84 (m, 1H), 6.70 (m, 2H), 6.49 (s, 1H), 6.19 (s, 1H), 4.84 (s, 2H), 3.80 (s, 3H), 3.40 (m, 1H), 3.16 (s, 3H), 3.02 (m, 1H), 2.72 (m, 4H), 1.32 (d, J=6.1 Hz, 3H).

Preparation of Compound (39)

To a solution of 25 (200 mg, 0.677 mmol) in DMF (15 mL) was added $K_2CO_3$ (280 mg, 2.03 mmol). The reaction mixture was stirred at room temperature for 15 minutes. Bromoacetonitrile (812 mg, 6.77 mmol) was added to the reaction mixture. The reaction mixture was heated at 80° C. for 18 hours. Most of the DMF was removed by rotary evaporation under reduced pressure and water (20 mL) was added. The aqueous phase was extracted with ethyl acetate (3×40 mL). The combined organic solvent was washed with water (20 mL) and dried over $MgSO_4$. The solvent was filtered and concentrated to dryness. The residue was purified by flash column chromatography (silica gel) using ethyl acetate/hexane (1/3) as an eluent to give the desired product (39) (204 mg, 90% yield); $^1$H-NMR ($CDCl_3$, 400 MHz) δ: 6.76 (m, 3H), 4.74 (s, 2H), 4.26 (m, 1H), 3.82 (s, 3H), 2.67 (m, 5H), 1.35 (m, 9H), 1.11 (m, 3H).

Preparation of Compound (40)

To a solution of 39 (50 mg, 0.15. mmol) in MeOH (8 mL) was added $CoCl_2$ $6H_2O$ (85 mg, 0.363 mmol). The reaction mixture was stirred at room temperature for minutes. $NaBH_4$ (58 mg, 1.53 mmol) was added to the reaction mixture. The reaction mixture was stirred for 2 hours and then filtered. The black precipitate formed from the reaction was washed with $CH_2Cl_2$ (3×10 mL). The combined organic phases were concentrated to dryness. The residue was purified by flash column chromatography (silica gel) using MeOH/$CH_2Cl_2$ (1/4) as an eluent to give the desired product (40) (11 mg) with recovery of starting material, 39. $^1$H-NMR ($CDCl_3$, 400 MHz) δ: 6.78 (m, 3H), 5.28 (m, NH), 4.51, 4.24 (m, 1H), 4.00 (m, 2H), 3.83 (s, 3H), 3.07 (m, 2H), 2.69 (m, 5H), 1.35 (m, 9H), 1.12 (m, 3H).

Preparation of Compound (50)

To a solution of MDMA (50 mg, 0.2177 mmol) in DMF (8 ml) was added NaH (30.7 mg, 1.21 mmol) and ethyl 5-bromovalerate (0.103 ml, 0.653 mmol). The reaction mixture was stirred and heated at 90° C. for 17 hours. DMF was removed by rotary evaporation and water (10 ml) was added. The aqueous phase was extracted with ethyl acetate (4×25 ml). The combined organic phase was washed with water (4×10 ml) and dried over $MgSO_4$, filtered and concentrated. The residue was purified by a preparative TLC using ethyl acetate/hexane (1/1) as an developing solvent first and MeOH/$CH_2Cl_2$ (1/9) to give the desired product (50) (36.5 mg, 52% yield). $^1$H-NMR ($CDCl_3$, 400 MHz) δ: 6.74 (d, J=7.8 Hz, 1H), 6.66 (s, 1H), 6.62 (d, J=7.9 Hz, 1H), 5.94 (s, 2H), 4.15 (q, J=7.13 Hz, 2H), 2.90 (m, 2H), 2.48 (t, J=7.3 Hz, 2H), 2.37–2.31 (m, 3H), 2.30 (s, 3H), 1.64 (m, 2H), 1.53 (m, 2H), 1.28 (t, J=7.13Hz, 3H), 0.94 (d, J=6.4, 3H).

Preparation of Compound (51)

To a solution of 50 (36.5 mg, 0.1137 mmol) in MeOH (5.0 ml) and $H_2O$ (0.5 ml) was added $K_2CO_3$ (159 mg, 1.15 mmol). The reaction mixture was stirred at room temperature for 16 hours. HCl (6N) was added to the mixture to adjust the pH=3–4. MeOH and water was evaporated by rotary evaporation under reduced pressure. The residue was dissolved in MeOH/$CH_2Cl_2$ (2/8) and $K_2CO_3$ was filtered. The organic solvent was removed by rotary evaporation and the residue was put in high vacuum to give the desired product (51) (35.9 mg, 96% yield). $^1$H-NMR ($CD_3OD$, 400 MHz) δ: 6.73 (m, 3H), 5.90 (s, 2H), 3.58 (m, 1H), 3.14 (t, J=7.3 Hz, 2H), 3.06 (m, 1H), 2.80 (s, 3H), 2.69 (m, 1H), 2.30 (t, J=6.7 Hz, 2H), 1.74 (m, 2H), 1.65 (m, 2H), 1.18 (d, J=6.6 Hz, 3H).

Preparation of MDMA-C5-KLH Immunogen (52)

To a solution of 51 (35.9 mg, 0.109 mmol) in THF (1.5 mL) was added DCC (26.9 mg, 0.13 mmol) and NHS (14 mg, 0.12 mmol). The reaction was stirred at room temperature for 16 hours. The precipitate from the reaction was filtered off and THF was removed by rotary evaporation. The activated hapten was dissolved in DMF (1 ml).

To a solution of KLH (20 mg, 8 ml, pH=8.00) was added the above activated hapten solution slowly at 4° C. under nitrogen. The pH value was maintained at 8.0. The reaction was stirred at 4° C. (cold room) for 16 hours. The reaction mixture was separated on the Sephadex G-25 column, which was equilibrated with $NaH_2PO_4$—$Na_2HPO_4$ buffer (pH=7.0, 0.1 M). The UV detector at 280 nm monitored the eluted fractions from the column. A clean separation between KLH immunogen and the hapten was obtained. Fractions containing protein were pooled and concentrated to 9 ml. The concentration of immunogen was measured by using BCA Protein Concentration Assay. The Immunogen (52) had a concentration of 1.89 mg/ml with a hapten number of 1108, and was used for the immunization of sheep, mice and rabbit for antibody production. Immunogen (53) was prepared in a manner similar to that described above for immunogen (52).

Figure 11:
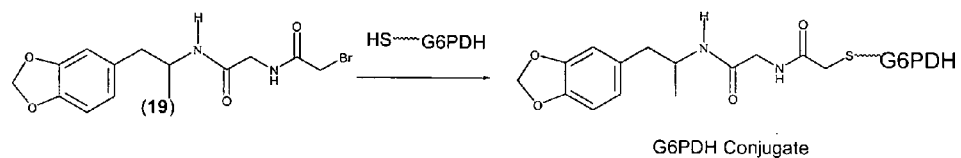
FIG. 11 is a reaction scheme depicting an example of the preparation of a G6PDH conjugate of MDA hapten (19).

Preparation of MDA Hapten (55) (FIG. 11)

To a MDA (4) (21.0 mg, 0.097 mmol) in THF (4 mL) solution was added N,N-diisopropyl ethyl amine (85 µL, 0.49 mmol). The mixture was stirred for half-hour under nitrogen before adding β-maleimidopropionic acid —NHS-ester (54) (38.9 mg, 0.146 mmol). The reaction was run under nitrogen at room temperature for one hour and forty minutes. The progress of the reaction was monitored by TLC with ethyl acetate as the developing solvent.

Most of organic solvent was removed by rotary evaporator. Trace amount of solvent was removed over high vacuum for one hour. Crude product (92.4 mg) was purified by flash column chromatography with MeOH/CH$_2$Cl$_2$ (2/98) as the eluent to give a white solid (55) (21.5 mg, 66% yield). $^1$H-NMR (CDCl$_3$, 400 MHz) δ: 6.66 (m, 5H), 5.93 (s, 2H), 5.45 (d, J=8 Hz, 1H), 4.16 (m, 1H), 3.81 (t, J=8, 2H), 2.67 (m, 2H), 2.47 (t, J=8, 2H), 1.08 (d, J=4.0 Hz, 3H).

Immunogens 10, 14, 30 and 36 were used to prepare antibodies according to methods similar to those described herein.

Preparation of Mutant G6PDH Conjugate from MDA Hapten (19)

Figure 10:
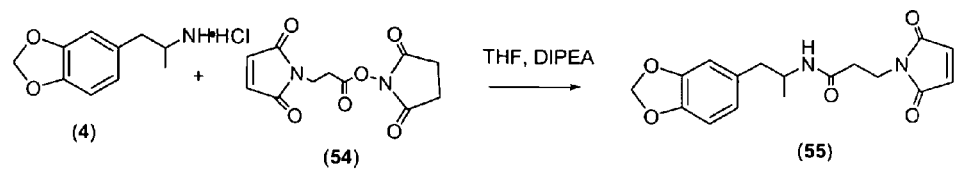
FIG. 10 is a reaction scheme depicting an example of the synthesis of MDA hapten (55).

Referring to FIG. 10, a mixture containing 5.5 mL mutant G6PDH, containing 27.5 mg protein, in 50 mM phosphate-1.0 mM EDTA, pH 7.25 and 55 µL of a solution of 0.5 M dithiothreitol in phosphate-EDTA buffer was incubated at 2–8° C. for 16 hours. The protein mixture was buffer exchanged with 50 mM phosphate-1.0 mM EDTA-25 µM DTT, pH 7.25 in an Amicon ultrafiltration system fitted with a YM10 membrane. Buffer exchange was continued until a mixture of 1.0 mL of the effluent and 20 µL of a dithiodipyridine (DTDP; 11.4 mg/10 mL of 10% alcohol) showed absorption at 324 nin identical to that of the mixture of DTDP solution with 1.0 mL of the phosphate-EDTA-DTT buffer. Number of sulfhydryls present in an aliquot of the protein was quantitated by reaction with DTDP and was found to be 1.0±0.5. A 0.2 mL dimethylformamide solution containing 7.0 mg hapten (19) was added to 4 mL of the protein solution containing 12 mg protein. Slightly turbid reaction mixture was shaken at 2–8° C. for 16 hr. Free hapten was separated from the hapten-enzyme conjugate by passage through a Sephadex G-50 column, prepared and eluted with 50 mM phosphate, pH 7.0. Protein-containing fractions of the conjugate were pooled based on absorption at 280 nm and stored at 2–8° C.

Haptens (15), (16), (17), (18), (20) and (38) were conjugated with G6PDH using a conjugation procedure similar to that described above.

Preparation of G6PDH Conjugate of Compound 34

To a solution of 34 (16.7 mg, 0.0565 mmol) in methanol (1 ml) was added K$_2$CO$_3$ (20 mg) and water (50 µL) under nitrogen. The reaction mixture was stirred at room temperature for 1.5 hour. The methanol was evaporated to dryness and the compound was dissolved in DMF (0.2 ml). To this solution was added bromoacetyl G6PDH (1.5 ml, 7.2 mg/ml, 10.8 mg protein) and 0.62 ml of 100 mM phosphate-5.0 mM EDTA, pH 7.60). The pH was adjusted from 7.41 to 7.70. The mixture was stirred at 4° C. for 16 hours. The mixture was centrifuged and filtered. The solution was diluted with 50 mM-phosphate and 100 mM NaCl, pH=7.0. The protein mixture was buffer exchanged with 50 mM phosphate-100 mM NaCl, pH 7.0 in an Amicon ultrafiltration system fitted with a YM10 membrane until negative reaction of DTDP was observed. This gave 3 ml of G6PDH conjugate of compound 34.

Figure 12:
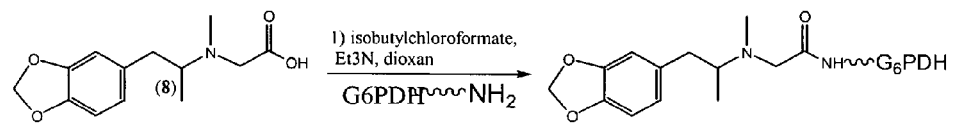
FIG. 12 is a reaction scheme depicting an example of the preparation of a G6PDH conjugate of Compound (8).

Preparation of G6PDH Conjugate from Compound 8 (FIG. 12)

A mixture of 8 (22.15 mg, 0.077 mmol) and triethyl amine (32.1 µL, 0.23 mmol) in dioxane (1 ml) was stirred at room temperature for 1 hour. The reaction was cooled in water bath. Isobutylchloroformate (15.7 µl, 0.115 mmol) was added to the reaction mixture. The mixture was stirred at room temperature for 1.5 hour. The 0.23 ml solution from the above reaction (0.0177 mmol, activated hapten) was added to a solution of G6PDH (2 mg/ml, 9.5 ml) in 100 mM phosphate, pH 7.0). The mixture was stirred at 4° C. for 16 hours. The protein mixture was buffer exchanged with 50 mM phosphate, pH 7.0 in an Amicon ultrafiltration system fitted with a YM10 membrane. This gave 2 ml of G6PDH conjugate (7.6 mg/ml, protein 15.2 mg).

Figure 13:
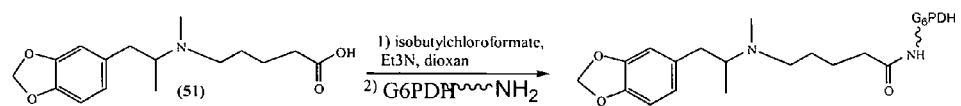
FIG. 13 is a reaction scheme depicting an example of the preparation of a G6PDH conjugate of Compound (51).

Preparation of G6PDH Conjugate from Compound 51 (FIG. 13)

A mixture of 51 (20.6 mg, 0.0626 mmol) and triethyl amine (26.0 µL, 0.186 mmol) in dioxane (1 ml) was stirred at room temperature for 1 hour. The reaction was cooled in water bath. Isobutylchloroformate (12.8 µL, 0.0941 mmol) was added to the reaction mixture. The mixture was stirred at room temperature for 1.5 hour. The 0.3 ml solution from the above reaction (0.0175 mmol, activated hapten) was added to a solution of G6PDH (2 mg/ml, 9.5 ml) in 100 mM phosphate, pH 7.0). The mixture was stirred at 4° C. for 16 hours. The protein mixture was buffer exchanged with 50 mM phosphate, pH 7.0 in an Amicon ultrafiltration system fitted with a YM10 membrane. This gave 2 ml of G6PDH conjugate (9.06 mg/ml, protein 18.1 mg).

Preparation of G6PDH Conjugates from Haptens 15, 16, 17, 19 and 20

G6PDH conjugates were prepared from haptens 15, 16, 17, 19 and 20 in a manner similar to that described above.

Assay using Reagents in Accordance with Embodiments of the Present Invention

The antibodies and enzyme conjugates in accordance with the invention may be employed in assays for the detection of the respective analytes. The immunogen (52) is injected into sheep to raise antibody. The antibody obtained from the sheep bleed is spiked into the antibody diluent to prepare the antibody reagent. The antibody reagent consists of antibody as prepared above, buffer, stabilizers, preservatives, and the substrates for the enzyme conjugate NAD and glucose 6 phosphate.

Enzyme conjugate comprising compound (19) and G6PDH is spiked into the conjugate reagent to prepare the enzyme conjugate reagent. The enzyme conjugate reagent consists of the conjugate, buffer, stabilizers and preservatives.

Figures 14, 15:
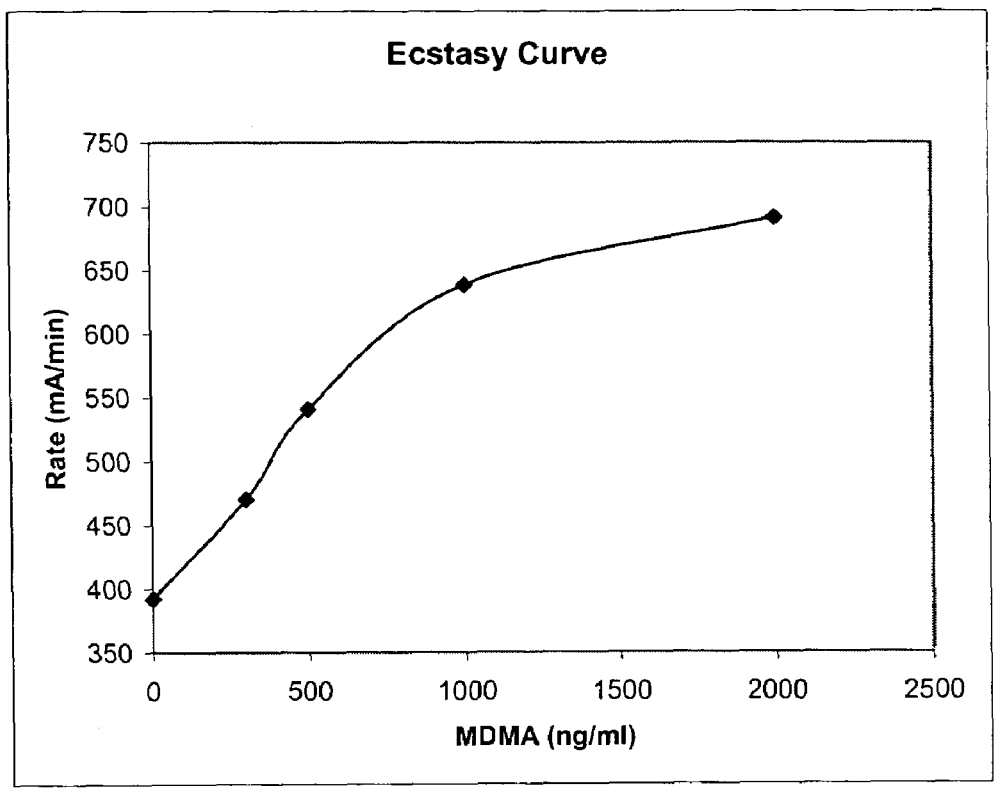
FIG. 14 is a graph depicting the results of an assay in accordance with the present invention.
FIG. 15 is a table showing the MDMA recovery from an assay in accordance with the present invention.

The antibody reagent and enzyme conjugate reagent are used in a homogeneous assay format to detect Ecstasy in urine samples. The analyzer (instrument) used to set up the assay is Syva 30-R Biochemical Analyzer (Syva Company, Cupertino Calif.). Ecstasy containing urine sample is incubated with antibody reagent followed by the addition of the enzyme conjugate reagent. The enzyme conjugate activity decreases upon binding to the antibody. The enzyme conjugate, which is not bound to the antibody, catalyzes the oxidation of glucose 6-phosphate (G6P). The oxidation of G6P is coupled with the reduction of $NAD^+$ to NADH, which can be measured at 340 nm. The change in the absorbance at 340 nm can be measured spectrophotometrically. The Ecstasy concentration in a urine specimen can be measured in terms of G6PDH activity. The increase in the rate at 340 nm is due to the formation of NADH and is proportional to the enzyme conjugate activity. An assay curve is generated using MDMA spiked into negative urine. The assay rate increases with increasing the concentration of free drug in the sample. Results are summarized in FIGS. 14 and 15.

The above discussion includes certain theories as to mechanisms involved in the present invention. These theories should not be construed to limit the present invention in any way, since it has been demonstrated that the present invention achieves the results described.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A compound of the formula:

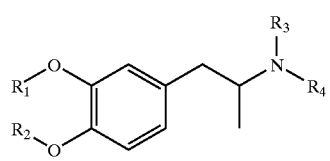

Formula I wherein: $R^1$ is H, lower alkyl, a protecting group, or is taken together with $R^2$ to form a ring,
$R^2$ is H, lower alkyl, a protecting group, —$(CH_2)_nSCH_2C(O)R^6$ or —$(CH_2)_nC(SO_2R^6)$=$CH_2$, or is taken together with $R^1$ to form a ring,
$R^3$ and $R^4$ are independently H or lower alkyl or a protecting group, or, when $R^1$ is taken together with $R^2$ to form a ring, at least one of $R^3$ or $R^4$ is —$C(O)(CH_2)_nR^5$, —$C(O)(CH_2)_nNHC(O)R^5$, —$C(O)(CH_2)_nNHC(O)(CH_2)_nSR^5$, —$(CH_2)_nC(SO_2R^5)$=$CH_2$, —$(CH_2)_nSCH_2C(O)R^5$, or —$(CH_2)_nC(SO_2R^5)$=$CH_2$, or when $R^1$ is not taken together with $R^2$ to form a ring, $R^2$ is not H or lower alkyl or a protecting group, $R^5$ is H, —OH, —SH, —O-lower alkyl, halogen, $NH_2$, -succinimidyl, -maleimidyl, immunogenic carrier, or label,
$R^6$ is H, —OH, —SH, —O-lower alkyl, halogen, $NH_2$, -succinimidyl, -maleimidyl, immunogenic carrier, or label, and
n is an integer from 1 to 5,
and including acid salts thereof.

2. A compound according to claim 1 wherein said immunogenic carrier is a poly(amino acid).

3. A compound according to claim 2 wherein said poly (amino acid) is a protein.

4. Antibodies raised against the compound of claim 3.

5. A compound according to claim 1 wherein n is 1.

6. A compound according to claim 1 wherein said label is an enzyme label, a luminescent label, or a radioisotope label.

7. A compound of the formula:

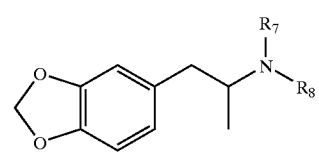

Formula II wherein: $R^7$ is H, lower alkyl, a protecting group, —$C(O)(CH_2)_nR^5$, —$C(O)(CH_2)_nNHC(O)R^5$, —$C(O)(CH_2)_nNHC(O)(CH_2)_nSR^5$, —$(CH_2)_nC(SO_2R^5)$=$CH_2$, —$(CH_2)_nSCH_2C(O)R^5$, or —$(CH_2)_nC(SO_2R^5)$=$CH_2$,
$R^8$ is H, lower alkyl, a protecting group, —$C(O)(CH_2)_nR^5$, —$C(O)(CH_2)_nNHC(O)R^5$, —$C(O)(CH_2)_nNHC(O)(CH_2)_nSR^5$, —$(CH_2)_nC(SO_2R^5)$=$CH_2$, —$(CH_2)_nSCH_2C(O)R^5$, or —$(CH_2)_nC(SO_2R^5)$=$CH_2$,
$R^5$ is H, —OH, —SH, —O-lower alkyl, halogen, $NH_2$, immunogenic carrier, -succinimidyl, -maleimidyl, or label, and
n is an integer from 1 to 5,
with the proviso that at least one of $R^7$ and $R^8$ are not H or lower alkyl, and including the acid salts thereof.

8. A compound according to claim 7 wherein said immunogenic carrier is a protein selected from the group consisting of KLH, BSA, BGG, and ovalbumin.

9. Antibodies raised against the compound of claim 8.

10. A compound according to claim 7 wherein n is 1.

11. A compound according to claim 6 wherein $R^7$ is H or lower alkyl.

12. A compound according to claim 7 wherein said label is an enzyme label, a luminescent label, or a radioisotope label.

13. A compound of the formula:

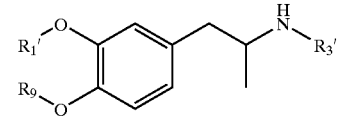

wherein: $R^{3'}$ is H, methyl or ethyl or a protecting group,
$R^{1'}$ is H or lower alkyl or a protecting group,
$R^9$ is a protecting group, —$(CH_2)_nSCH_2C(O)R^6$ or —$(CH_2)_nC(SO_2R^6)$=$CH_2$, $R^6$ is H, —OH, —SH, —O-lower alkyl, halogen, $NH_2$, immunogenic carrier, -succinimidyl, -maleimidyl, or label, and
n is an integer from 1 to 5, and including acid salts thereof.

14. A compound according to claim 13 wherein said protein is selected from the group consisting of KLH, BSA, BGG, and ovalbumin.

15. Antibodies raised against the compound of claim 14.

16. A compound according to claim 13 wherein n is 1.

17. A compound according to claim 13 wherein said label is an enzyme label, a luminescent label, or a radioisotope label.

18. A method for determining a compound selected from the group consisting of 3,4-methylenedioxyamphetamine (MDA), 3,4-methylenedioxy-methamphetamine (MDMA), 3,4-methylenedioxyethylamphetamine (MDEA) and 4-hydroxy-3-methoxy-methamphetamine (HMMA), said method comprising:
(a) providing in combination in a medium:
(i) a sample suspected of containing said compound and
(ii) an antibody raised against a compound of the formula:

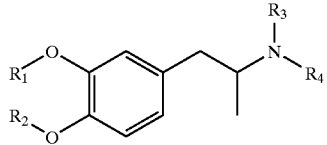

wherein: $R^1$ is H, lower alkyl, a protecting group, or is taken together with $R^2$ to form a ring,
$R^2$ is H, lower alkyl, a protecting group, $-(CH_2)_nSCH_2C(O)R^6$ or $-(CH_2)_nC(SO_2R^6)=CH_2$, or is taken together with $R^1$ to form a ring,
$R^3$ and $R^4$ are independently H or lower alkyl or a protecting group, or, when $R^1$ is taken together with $R^2$ to form a ring, at least one of $R^3$ or $R^4$ is $-C(O)(CH_2)_nR^5$, $-C(O)(CH_2)_nNHC(O)R^5$, $-C(O)(CH_2)_nNHC(O)(CH_2)_nSR^5$, $-(CH_2)_nC(SO_2R^5)=CH_2$, $-(CH_2)_nSCH_2C(O)R^5$, or $-(CH_2)_nC(SO_2R^5)=CH_2$, or when $R^1$ is not taken together with $R^2$ to form a ring, $R^2$ is not H or lower alkyl or a protecting group,
$R^5$ is an immunogenic carrier,
$R^6$ is an immunogenic carrier, and
n is an integer from 1 to 5, and
(b) examining said medium for the presence a complex comprising said compound and said antibody, the presence thereof indicating the presence of said compound in said sample.

19. A method according to claim 18 wherein said combination further comprises:
(iii) a label conjugate of the formula:

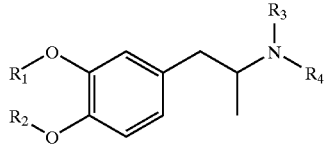

wherein: $R^1$ is H, lower alkyl, a protecting group, or is taken together with $R^2$ to form a ring,
$R^2$ is H, lower alkyl, a protecting group, $-(CH^2)_nSCH_2C(O)R^6$ or $-(CH_2)_nC(SO_2R^6)=CH_2$, or is taken together with $R^1$ to form a ring,
$R^3$ and $R^4$ are independently H or lower alkyl or a protecting group, or, when $R^1$ is taken together with $R^2$ to form a ring, at least one of $R^3$ or $R^4$ is $-C(O)(CH_2)_nR^5$, $-C(O)(CH_2)_nNHC(O)R^5$, $-C(O)(CH_2)_nNHC(O)(CH_2)_nSR^5$, $-(CH_2)_nC(SO_2R^5)=CH_2$, $-(CH_2)_nSCH_2C(O)R^5$, or $-(CH_2)_nC(SO_2R^5)=CH_2$, or when $R^1$ is not taken together with $R^2$ to form a ring, $R^2$ is not H or lower alkyl or a protecting group,
$R^5$ is a label,
$R^6$ is a label, and
n is an integer from 1 to 5, and
said examining comprises measuring signal from said label, the amount thereof being related to the presence of said compound in said sample.

20. A method according to claim 19 wherein said method is a homogeneous method and said medium is examined for the amount of said signal.

21. A method according to claim 18 wherein said method is a heterogeneous method and said complex, if present, is separated from said medium.

22. A method according to claim 18 wherein said protein is selected from the group consisting of KLH, BSA, BGG and ovalbumin.

23. A method according to claim 18 wherein n is 1.

24. A method according to claim 19 wherein said label is an enzyme label, a luminescent label, or a radioisotope label.

25. A kit for determining a compound selected from the group consisting of 3,4-methylenedioxyamphetamine (MDA), 3,4-methylenedioxy-methamphetamine (MDMA), 3,4-methylenedioxyethylamphetamine (MDEA) and 4-hydroxy-3-methoxy-methamphetamine (HMMA), said kit comprising:
(a) an antibody raised against a compound of the formula:

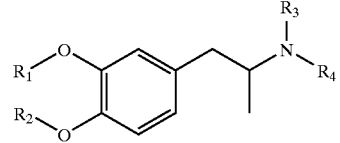

wherein: $R^1$ is H, lower alkyl, a protecting group, or is taken together with $R^2$ to form a ring,
$R^2$ is H, lower alkyl, a protecting group, $-(CH^2)_nSCH_2C(O)R^6$ or $-(CH_2)_nC(SO_2R^6)=CH_2$, or is taken together with $R^1$ to form a ring,
$R^3$ and $R^4$ are independently H or lower alkyl or a protecting group, or, when $R^1$ is taken together with $R^2$ to form a ring, at least one of $R^3$ or $R^4$ is $-C(O)(CH_2)_nR^5$, $-C(O)(CH_2)_nNHC(O)R^5$, $-C(O)(CH_2)_nNHC(O)(CH_2)_nSR^5$, $-(CH_2)_nC(SO_2R^5)=CH_2$, $-(CH_2)_nSCH_2C(O)R^5$, or $-(CH_2)_nC(SO_2R^5)=CH_2$, or when $R^1$ is not taken together with $R^2$ to form a ring, $R^2$ is not H or lower alkyl or a protecting group,
$R^5$ is an immunogenic carrier,
$R^6$ is an immunogenic carrier, and
n is an integer from 1 to 5, and
(b) ancillary reagents for determining said compound.

26. A kit for determining a compound selected from the group consisting of 3,4-methylenedioxyamphetamine (MDA), 3,4-methylenedioxy-methamphetamine (MDMA), 3,4-methylenedioxyethylamphetamine (MDEA) and 4-hydroxy-3-methoxy-methamphetamine (HMMA), said kit comprising:
(a) an antibody for said compound, (b) a label conjugate of the formula:

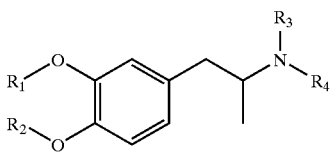

Formula V wherein: $R^1$ is H, lower alkyl, a protecting group, or is taken together with $R^2$ to form a ring, $R^2$ is H, lower alkyl, a protecting group, $-(CH_2)_nSCH_2C(O)R^6$ or $-(CH_2)_nC(SO_2R^6)=CH_2$, or is taken together with $R^1$ to form a ring, $R^3$ and $R^4$ are independently H or lower alkyl or a protecting group, or, when $R^1$ is taken together with $R^2$ to form a ring, at least one of $R^3$ or $R^4$ is $-C(O)(CH_2)_nR^5$, $-C(O)(CH_2)_nNHC(O)R^5$, $-C(O)(CH_2)_nNHC(O)(CH_2)_nSR^5$, $-(CH_2)_nC(SO_2R^5)=CH_2$, $-(CH_2)_nSCH_2C(O)R^5$, or $-(CH_2)_nC(SO_2R^5)=CH_2$, or when $R^1$ is not taken together with $R^2$ to form a ring, $R^2$ is not H or lower alkyl or a protecting group, $R^5$ is a label, $R^6$ is a label, and n is an integer from 1 to 5, and (c) ancillary reagents for determining said compound.

27. A kit according to claim 25 wherein said protein is selected from the group consisting of KLH, BSA, BGG and ovalbumin.

28. A kit according to claim 25 wherein n is 1.

29. A kit according to claim 26 wherein said label is an enzyme label, a luminescent label, or a radioisotope label.

30. A method for determining amphetamine and/or methamphetamine and/or methylenedioxyethamphetamine in a sample suspected of containing methylenedioxyamphetamine and/or methylenedioxymethamphetamine and/or methylenedioxyethamphetamine, said method comprising:

(a) providing in combination in a medium:
  (i) said sample,
  (ii) an antibody for methylenedioxyamphetamine, and/or
  (iii) an antibody for methylenedioxymethamphetamine, and/or
  (iv) an antibody for methylenedioxyethamphetamine, and
  (v) a compound of the formula:

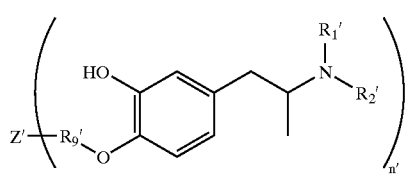

wherein:
$R^{1\prime}$ is H,
$R^{2\prime}$ is H, or methyl or ethyl,
$R^{9\prime}$ is $-(CH_2)_nSCH_2C(O)R^{6\prime}$ or $-(CH_2)_nC(SO_2R^{6\prime})=CH_2$,
$R^{6\prime}$ is Z', which is an enzyme,
n' is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

31. A method for determining methylenedioxyamphetamine and/or methylenedioxymethamphetamine and/or methylenedioxyethamphetamine in a sample suspected of containing methylenedioxyamphetamine and/or methylenedioxymethamphetamine and/or methylenedioxyethamphetamine, said method comprising:

(a) providing in combination in a medium:
  (i) said sample,
  (ii) an antibody for methylenedioxyamphetamine, and/or
  (iii) an antibody for methylenedioxymethamphetamine, and/or
  (iv) an antibody for methylenedioxyethamphetamine, and
  (v) a compound of the formula:

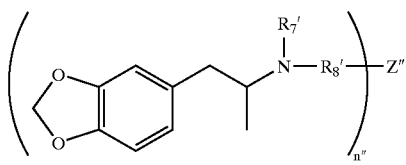

wherein:
$R^{7\prime}$ is H, or methyl, or ethyl,
$R^{8\prime}$ is $-C(O)(CH_2)_nR^{5\prime}$, $-C(O)(CH_2)_nNHC(O)R^{5\prime}$, $-C(O)(CH_2)_nNHC(O)(CH_2)_nSR^5$, $-(CH_2)_nC(SO_2R^{5\prime})=CH_2$, $-(CH_2)_nSCH_2C(O)R^{5\prime}$ or $-(CH_2)_nC(SO_2R^{5\prime})=CH_2$,
$R^{5\prime}$ is Z", which is an enzyme,
n" is an integer between 1 and the molecular weight of said enzyme divided by about 500; and (b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxymethamphetamine in said sample.

32. A method for determining methylenedioxyamphetamine and/or methylenedioxymethamphetamine and/or methylenedioxyethamphetamine in a sample suspected of containing methylenedioxyamphetamine and/or methylenedioxymethamphetamine and/or methylenedioxyethamphetamine, said method comprising:

(a) providing in combination in a medium:
  (i) said sample,
  (ii) a conjugate of an enzyme and a methylenedioxyamphetamine analog and/or a conjugate of an enzyme and a methylenedioxymethamphetamine analog and/or a conjugate of an enzyme and a methylenedioxyethamphetamine analog,
(iii) an antibody for methylenedioxyamphetamine, said antibody being raised against a compound of the formula:

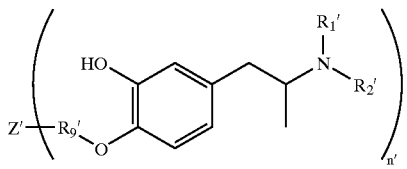

wherein:
$R^{1\prime}$ is H,
$R^{2\prime}$ is H,
$R^{9\prime}$ is $-(CH_2)_nSCH_2C(O)R^{6\prime}$ or $-(CH_2)_nC(SO_2R^{6\prime})=CH_2$,
$R^{6\prime}$ is Z', which is a protein immunogenic carrier or a non-poly(amino acid) immunogenic carrier,
n' is an integer between 1 and the molecular weight of said protein immunogenic carrier or said non-ploy(amino acid) immunogenic carrier divided by about 500; and/or
(iv) an antibody for methylenedioxymethamphetamine, said antibody being raised against a compound of the formula:

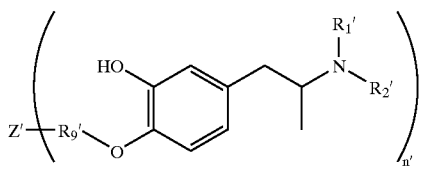

wherein:
$R^{1\prime}$ is H,
$R^{2\prime}$ is methyl,
$R^{9\prime}$ is $-(CH_2)_nSCH_2C(O)R^{6\prime}$ or $-(CH_2)_nC(SO_2R^{6\prime})=CH_2$,
$R^{6\prime}$ is Z', which is a protein immunogenic carrier or a non-poly(amino acid) immunogenic carrier,
n' is an integer between 1 and the molecular weight of said protein immunogenic carrier or said non-poly(amino acid) immunogenic carrier divided by about 500; and/or
(v) an antibody for methylenedioxyethamphetamine, said antibody being raised against a compound of the formula:

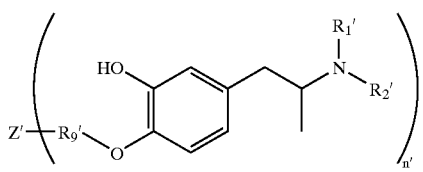

wherein:
$R^{1\prime}$ is H,
$R^{2\prime}$ is ethyl,
$R^{9\prime}$ is $-(CH_2)_nSCH_2C(O)R^{6\prime}$ or $-(CH_2)_nC(SO_2R^{6\prime})=CH_2$,
$R^{6\prime}$ is Z', which is a protein immunogenic carrier or a non-poly(amino acid) immunogenic carrier,
n' is an integer between 1 and the molecular weight of said protein immunogenic carrier or said non-poly(amino acid) immunogenic carrier divided by about 500; and
(b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said methylenedioxyamphetamine and/or methylenedioxymethamphetamine and/or methylenedioxyethamphetamine in said sample.

33. A method for determining methylenedioxyamphetamine and/or methylenedioxymethamphetamine in a sample suspected of containing methylenedioxyamphetamine and/or methylenedioxymethamphetamine, said method comprising:
(a) providing in combination in a medium:
(i) said sample,
(ii) a conjugate of an enzyme and an methylenedioxyamphetamine analog and/or a conjugate of an enzyme and a methylenedioxymethamphetamine analog and/or a conjugate of an enzyme and a methylenedioxyethamphetamine analog,
(iii) an antibody for methylenedioxyamphetamine, said antibody being raised against a compound of the formula:

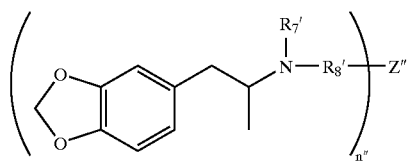

wherein:
$R^{7\prime}$ is H,
$R^{8\prime}$ is $-C(O)(CH_2)_nR^5$, $-C(O)(CH_2)_nNHC(O)R^5$, $-C(O)(CH_2)_nNHC(O)(CH_2)_nSR^5$, $-(CH_2)_nC(SO_2R^5)=CH_2$, $-(CH_2)_nSCH_2C(O)R^5$ or $-(CH_2)_nC(SO_2R^5)=CH_2$,
$R^{5\prime}$ is Z", which is a protein immunogenic carrier or a non-poly(amino acid) immunogenic carrier,
n" is an integer between 1 and the molecular weight of said protein immunogenic carrier or said non-poly(amino acid) immunogenic carrier divided by about 500; and/or (iv) an antibody for methylenedioxymethamphetamine, said antibody being raised against a compound of the formula:

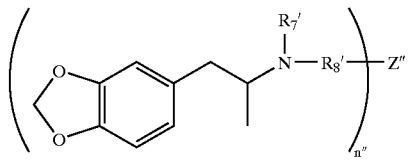

wherein:
R$^{7'}$ is methyl,
R$^{8'}$ is —C(O)(CH$_2$)$_n$R$^{5'}$, —C(O)(CH$_2$)$_n$NHC(O)R$^5$, —C(O)(CH$_2$)$_n$NHC(O)(CH$_2$)$_n$SR$^5$, —(CH$_2$)$_n$C(SO$_2$R$^{5'}$)=CH$_2$, —(CH$_2$)$_n$SCH$_2$C(O)R$^{5'}$ or —(CH$_2$)$_n$C(SO$_2$R$^{5'}$)=CH$_2$,
R$^{5'}$ is Z″, which is a protein immunogenic carrier or a non-poly(amino acid) immunogenic carrier,
n″ is an integer between 1 and the molecular weight of said protein immunogenic carrier or said non-poly(amino acid) immunogenic carrier divided by about 500; and/or
(v) an antibody for methylenedioxyethamphetamine, said antibody being raised against a compound of the formula:

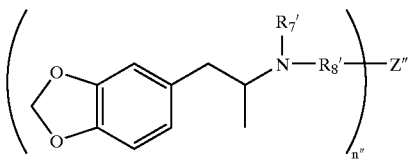

wherein:
R$^{7'}$ is ethyl,
R$^{8'}$ is —C(O)(CH$_2$)$_n$R$^{5'}$, —C(O)(CH$_2$)$_n$NHC(O)R$^{5'}$, —C(O)(CH$_2$)$_n$NHC(O)(CH$_2$)$_n$SR$^5$, —(CH$_2$)$_n$C(SO$_2$R$^{5'}$)=CH$_2$, —(CH$_2$)$_n$SCH$_2$C(O)R$^{5'}$ or —(CH$_2$)$_n$C(SO$_2$R$^{5'}$)=CH$_2$,
R$^{5'}$ is Z″, which is a protein immunogenic carrier or a non-poly(amino acid) immunogenic carrier,
n″ is an integer between 1 and the molecular weight of said protein immunogenic carrier or said non-poly(amino acid) immunogenic carrier divided by about 500; and
(b) examining said medium for the presence of a complex comprising said methylenedioxyamphetamine and said antibody for methylenedioxyamphetamine and/or a complex of said methylenedioxymethamphetamine and said antibody for methylenedioxymethamphetamine and/or a complex of said methylenedioxyethamphetamine and said antibody for methylenedioxyethamphetamine, the presence thereof indicating the presence of said amphetamine and/or methamphetamine and/or methylenedioxyethamphetamine in said sample.

34. A kit comprising in packaged combination:
  (i) an antibody for methylenedioxyamphetamine, and/or
  (ii) an antibody for methylenedioxymethamphetamine, and/or
  (iii) an antibody for methylenedioxyethamphetamine, and (iv) a compound of the formula:

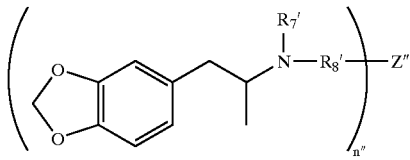

wherein:
R$^{7'}$ is H, or methyl, or ethyl,
R$^{8'}$ is —C(O)(CH$_2$)$_n$R$^{5'}$, —C(O)(CH$_2$)$_n$NHC(O)R$^{5'}$, —C(O)(CH$_2$)$_n$NHC(O)(CH$_2$)$_n$SR$^5$, —(CH$_2$)$_n$C(SO$_2$R$^{5'}$)=CH$_2$, —(CH$_2$)$_n$SCH$_2$C(O)R$^{5'}$ or —(CH$_2$)$_n$C(SO$_2$R$^{5'}$)=CH$_2$,
R$^{5'}$ is Z″, which is an enzyme,
n″ is an integer between 1 and the molecular weight of said enzyme divided by about 500.

35. A kit comprising in packaged combination:
  (i) an antibody for methylenedioxyamphetamine,
  (ii) an antibody for methylenedioxymethamphetamine, and/or
  (iii) an antibody for methylenedioxyethamphetamine, and
  (iv) a compound of the formula:

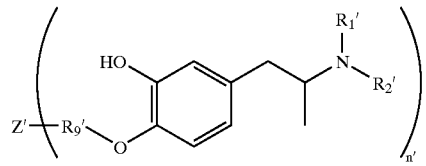

wherein:
R$^{1'}$ is H,
R$^{2'}$ is H, or methyl or ethyl,
R$^{9'}$ is —(CH$_2$)$_n$SCH$_2$C(O)R$^{6'}$ or —(CH$_2$)$_n$C(SO$_2$R$^{6'}$)=CH$_2$,
R$^{6'}$ is Z', which is an enzyme,
n' is an integer between 1 and the molecular weight of said enzyme divided by about 500.

36. A kit comprising in packaged combination:
  (i) a conjugate of an enzyme and a methylenedioxyamphetamine analog and/or a conjugate of an enzyme and a methylenedioxymethamphetamine analog, and/or a conjugate of an enzyme and a methylenedioxyethamphetamine analog, and
  (ii) an antibody for methylenedioxyamphetamine, said antibody being raised against a compound of the formula:

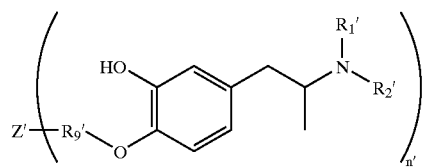

wherein:
R$^{1'}$ is H,
R$^{2'}$ is H, $R^{9'}$ is —(CH$_2$)$_n$SCH$_2$C(O)R$^{6'}$ or —(CH$_2$)$_n$C(SO$_2$R$^{6'}$)=CH$_2$, $R^{6'}$ is Z', which is a protein immunogenic carrier or a non-poly(amino acid) immunogenic carrier, n' is an integer between 1 and the molecular weight of said protein immunogenic carrier or said non-poly(amino acid) immunogenic carrier divided by about 500; and/or (iii) an antibody for methylenedioxymethamphetamine, said antibody being raised against a compound of the formula:

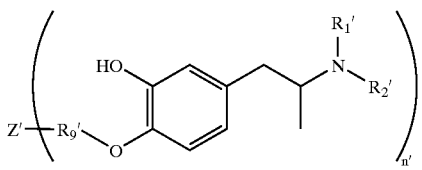

wherein:
$R^{1'}$ is H,
$R^{2'}$ is methyl,
$R^{9'}$ is —(CH$_2$)$_n$SCH$_2$C(O)R$^{6'}$ or —(CH$_2$)$_n$C(SO$_2$R$^{6'}$)=CH$_2$,
$R^{6'}$ is Z', which is a protein immunogenic carrier or a non-poly(amino acid) immunogenic carrier,
n' is an integer between 1 and the molecular weight of said protein immunogenic carrier or said non-poly(amino acid) immunogenic carrier divided by about 500, and/or (iv) an antibody for methylenedioxyethamphetamine, said antibody being raised against a compound of the formula:

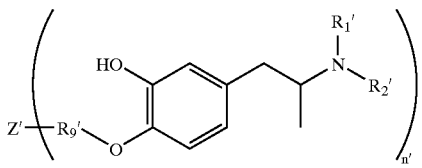

wherein:
$R^{1'}$ is H,
$R^{2'}$ is ethyl,
$R^{9'}$ is —(CH$_2$)$_n$SCH$_2$C(O)R$^{6'}$ or —(CH$_2$)$_n$C(SO$_2$R$^{6'}$)=CH$_2$,
$R^{6'}$ is Z', which is a protein immunogenic carrier or a non-poly(amino acid) immunogenic carrier,
n' is an integer between 1 and the molecular weight of said protein immunogenic carrier or said non-poly(amino acid) immunogenic carrier divided by about 500.

37. A kit comprising in packaged combination:
(i) a conjugate of an enzyme and a methylenedioxyamphetamine analog and/or a conjugate of an enzyme and a methylenedioxymethamphetamine analog, and/or a conjugate of an enzyme and a methylenedioxyethamphetamine analog, and
(ii) an antibody for methylenedioxyamphetamine, said antibody being raised against a compound of the formula:

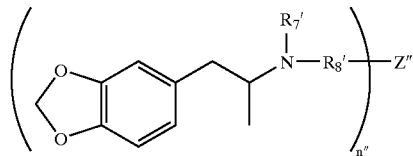

wherein:
$R^{7'}$ is H,
$R^{8'}$ is —C(O)(CH$_2$)$_n$R$^{5'}$, —C(O)(CH$_2$)$_n$NHC(O)R$^{5'}$, —C(O)(CH$_2$)$_n$NHC(O)(CH$_2$)$_n$SR$^5$, —(CH$_2$)$_n$C(SO$_2$R$^{5'}$)=CH$_2$, —(CH$_2$)$_n$SCH$_2$C(O)R$^{5'}$ or —(CH$_2$)$_n$C(SO$_2$R$^{5'}$)=CH$_2$,
$R^{5'}$ is Z", which is a protein immunogenic carrier or a non-poly(amino acid) immunogenic carrier,
n" is an integer between 1 and the molecular weight of said protein immunogenic carrier or said non-poly(amino acid) immunogenic carrier divided by about 500; and/or (iii) an antibody for methylenedioxymethamphetamine, said antibody being raised against a compound of the formula:

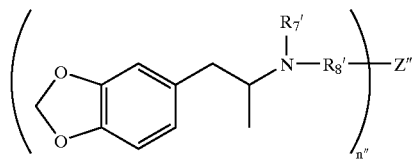

wherein:
$R^{7'}$ is methyl,
$R^{8'}$ is —C(O)(CH$_2$)$_n$R$^{5'}$, —C(O)(CH$_2$)$_n$NHC(O)R$^{5'}$, —C(O)(CH$_2$)$_n$NHC(O)(CH$_2$)$_n$SR$^5$, —(CH$_2$)$_n$C(SO$_2$R$^{5'}$)=CH$_2$, —(CH$_2$)$_n$SCH$_2$C(O)R$^{5'}$ or —(CH$_2$)$_n$C(SO$_2$R$^{5'}$)=CH$_2$,
$R^{5'}$ is Z", which is a protein immunogenic carrier or a non-poly(amino acid) immunogenic carrier,
n" is an integer between 1 and the molecular weight of said protein immunogenic carrier or said immunogenic carrier divided by about 500, and/or (iv) an antibody for methylenedioxyethamphetamine, said antibody being raised against a compound of the formula:

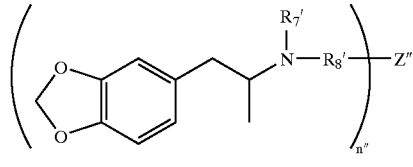

wherein:
$R^{7'}$ is ethyl,
$R^{8'}$ is —C(O)(CH$_2$)$_n$R$^5$, —C(O)(CH$_2$)$_n$NHC(O)R$^{5'}$, —C(O)(CH$_2$)$_n$NHC(O)(CH$_2$)$_n$SR$^5$, —(CH$_2$)$_n$C(SO$_2$R$^{5'}$)=CH$_2$, —(CH$_2$)$_n$SCH$_2$C(O)R$^{5'}$ or —(CH$_2$)$_n$C(SO$_2$R$^{5'}$)=CH$_2$,
$R^{5'}$ is Z", which is a protein immunogenic carrier or a non-poly(amino acid) immunogenic carrier,
n" is an integer between 1 and the molecular weight of said protein immunogenic carrier or said non-poly(amino acid) immunogenic carrier divided by about 500.

* * * * *